(12) United States Patent
Ramer et al.

(10) Patent No.: US 11,389,566 B2
(45) Date of Patent: Jul. 19, 2022

(54) METHOD AND COMPOSITION FOR TREATING INFLAMMATORY BOWEL DISEASE

(71) Applicants: Regentys Corporation, Miami Lakes, FL (US); University of Pittsburgh—of the Commonwealth System of Higher Education, Pittsburgh, PA (US)

(72) Inventors: Marc Ramer, Weston, FL (US); Stephen F. Badylak, Pittsburgh, PA (US); Timothy Keane, Wellsboro, PA (US)

(73) Assignees: Regentys Corporation, Miami Lakes, FL (US); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 697 days.

(21) Appl. No.: 16/085,001

(22) PCT Filed: Mar. 14, 2017

(86) PCT No.: PCT/US2017/022363
§ 371 (c)(1),
(2) Date: Sep. 14, 2018

(87) PCT Pub. No.: WO2017/160878
PCT Pub. Date: Sep. 21, 2017

(65) Prior Publication Data
US 2019/0076574 A1    Mar. 14, 2019

Related U.S. Application Data

(60) Provisional application No. 62/308,102, filed on Mar. 14, 2016.

(51) Int. Cl.
| | | |
|---|---|---|
| A61L 27/36 | (2006.01) | |
| A61L 27/38 | (2006.01) | |
| A61L 27/52 | (2006.01) | |
| A61P 1/00 | (2006.01) | |
| A61K 35/22 | (2015.01) | |
| A61K 35/38 | (2015.01) | |
| A61L 27/54 | (2006.01) | |

(52) U.S. Cl.
CPC .......... *A61L 27/3633* (2013.01); *A61K 35/22* (2013.01); *A61K 35/38* (2013.01); *A61L 27/36* (2013.01); *A61L 27/3629* (2013.01); *A61L 27/3679* (2013.01); *A61L 27/3834* (2013.01); *A61L 27/52* (2013.01); *A61L 27/54* (2013.01); *A61P 1/00* (2018.01)

(58) Field of Classification Search
None
See application file for complete search history.

(56) References Cited

U.S. PATENT DOCUMENTS

| | | | |
|---|---|---|---|
| 4,902,508 A | | 2/1990 | Badylak et al. |
| 4,956,178 A | * | 9/1990 | Badylak ............... A61L 27/3629 424/551 |
| 5,275,826 A | | 1/1994 | Badylak |
| 5,554,389 A | * | 9/1996 | Badylak ............... C12N 5/0068 424/558 |
| 5,817,662 A | | 10/1998 | Klein |
| 5,885,619 A | | 3/1999 | Patel |
| 6,576,265 B1 | | 6/2003 | Spievack |
| 6,890,564 B2 | | 5/2005 | Spievack |
| 8,021,692 B2 | | 9/2011 | Hiles et al. |
| 8,361,503 B2 | | 1/2013 | Badylak et al. |
| 8,673,362 B2 | | 3/2014 | Girsh |
| 8,691,276 B2 | | 4/2014 | Badylak et al. |
| 8,716,438 B2 | | 5/2014 | Agrawal et al. |
| 8,741,352 B2 | | 6/2014 | Hodde et al. |
| 8,802,436 B1 | | 8/2014 | Kentner et al. |
| 8,895,304 B2 | | 11/2014 | Fette et al. |
| 8,906,631 B2 | | 12/2014 | Clevers et al. |
| 8,975,075 B2 | | 3/2015 | Fette et al. |
| 9,079,965 B2 | | 7/2015 | Zhou et al. |
| 9,186,435 B2 | | 11/2015 | Hiles |
| 9,433,701 B2 | * | 9/2016 | Spievack ............ A61L 27/3604 |
| 9,538,996 B2 | | 1/2017 | Patel |
| 2012/0114755 A1 | | 5/2012 | Amadio et al. |
| 2012/0264190 A1 | | 10/2012 | Christman et al. |
| 2014/0271491 A1 | | 9/2014 | Gittard et al. |
| 2016/0045552 A1 | | 2/2016 | Ramer et al. |

FOREIGN PATENT DOCUMENTS

| | | |
|---|---|---|
| JP | 2011-246461 | 12/2011 |
| WO | WO 1994/011008 | 5/1994 |
| WO | WO 1998/9801112 | 1/1998 |
| WO | WO 2012/064606 | 11/2011 |
| WO | WO 2012/114333 | 8/2012 |
| WO | WO 2014/144215 | 9/2014 |

OTHER PUBLICATIONS

Naba, et al. (2014) "Extracellular matrix signatures of human primary metastatic colon cancers and their metastases to liver", BMC Cancer, 14: article 518, 12 pages as printed. (Year: 2014).*
Hurlstone, David P., Endoscopic mucosal resection for flat neoplasia in chronic ulcerative colitis: can we change the endoscopic management paradigm?, Gut, Nov. 27, 2006, vol. 56, pp. 838-846.
Lanzoni, et al., Inflammatory bowel disease: Moving Toward a stem cell-based therapy. World J. Gasstroenterol. Aug. 7, 2008, vol. 14, No. 29. pp 4616-4626.

(Continued)

*Primary Examiner* — Robert M Kelly
(74) *Attorney, Agent, or Firm* — Ted Whitlock

(57) ABSTRACT

Methods and compositions for treating diseased or damaged tissue, such as Inflammatory Bowel Disease, e.g., Ulcerative Colitis, include tissue regeneration using stem cells or tissue grafts which stimulate stem cell migration to the damaged tissue. The tissue grafts can be extracellular matrix (ECM) material, such as tissue-specific extracellular matrix (TS-ECM). The methods can also include mucosal resection of the damaged or diseased tissue prior to placement of the graft.

9 Claims, 13 Drawing Sheets
(6 of 13 Drawing Sheet(s) Filed in Color)

(56) References Cited

OTHER PUBLICATIONS

Markel, et al., Stem Cells as a Potential Future Treatment of Pediatric Intestinal Disorders. J. Pediatr. Surg. Nov. 2008, vol. 43, No. 11, pp. 1953-1963.
Hoeppner, J., et al., Small Intestine Submucosa as a Bioscaffold for Tissue Regeneration in Defects of the Colonic Wall, J. Gastroentest.. Surg., 2009 vol. 13, pp. 113-119.
Cornwell, K. G., et al., Extracellular Matrix Biomaterials for Soft Tissue Repair, Clin Podiatr. Med. Surg. No. 26 (2009), pp. 507-509.
Zhou, et al., Localized colonic stem cell transplantation enhances tissue regeneration in murine colitis. J. Mol. Med. Aug. 2012. vol 16, No. 8 pp. 1900-1915.
International Search Report and Written Opinion dated Sep. 8, 2014 in WO 2014/168964.
State of the Art Cure of Ulcerative Colitis in Kiev Ukraine (undated) https://www.placidway.com/package/1089/State-Of-The-Art-Cure-of-Ulcerative-Colitis-in-Kiev-Ukraine.
Chen et al., "Small Bowel Tissue Engineering Using Small Intestinal Submucosa as a Scaffold," Journal of Surgical Research, 2001, vol. 99, No. 2, pp. 352-358.
Demirbilek et al., "Using porcine small intestinal submucosa in intestinal regeneration," Pediatric Surgery International, 2003, vol. 19, No. 8, pp. 588-592.

* cited by examiner

PIVOTAL RAT STUDY DESIGN AND MEASUREMENTS

Table 1. Criteria for clinical symptom scoring

| Score | Weight loss | Stool consistency | Stool Blood |
|---|---|---|---|
| 0 | None | Normal | None |
| 1 | 1-5% | | |
| 2 | 5-10% | Loose stools | Occult |
| 3 | 10-20% | | |
| 4 | >20% | Diarrhea | Gross bleeding |

Table 2. Criteria for gross anatomical scoring of colon specimens

| Score | Appearance |
|---|---|
| 0 | Normal |
| 1 | Localized hyperemia, no ulcers |
| 2 | Ulceration without hyperemia or bowel wall thickening |
| 3 | Ulceration with inflammation at one site |
| 4 | Two or more sites of ulceration and inflammation |
| 5 | Ulceration at multiple sites or extending >1 cm along the length of the colon |
| 6-10 | When an area of damage extended >2 cm along the length of colon, the score was increased by 1 for each additional cm of involvement |

Table 3. Criteria for histologic scoring of colon specimens

| Feature | Score | Description |
|---|---|---|
| Inflammation extent | 0 | No inflammation |
| | 1 | Mild inflammation in mucosa |
| | 2 | Moderate-severe inflammation in mucosa |
| | 3 | Mild inflammation into the submucosa |
| | 4 | Moderate-severe inflammation into the submucosa |
| Ulceration | 0 | 0% |
| | 1 | 1-25% |
| | 2 | 26-50% |
| | 3 | 51-75% |
| | 4 | 76-100% |

FIG. 3

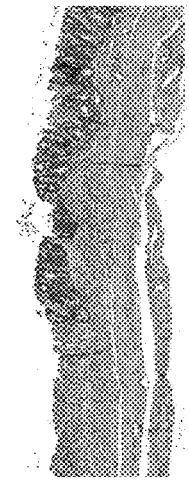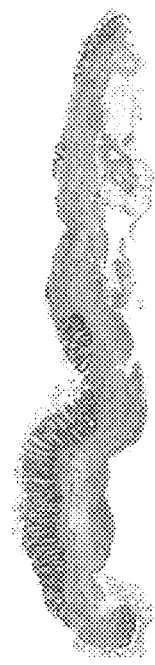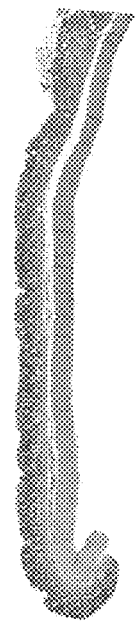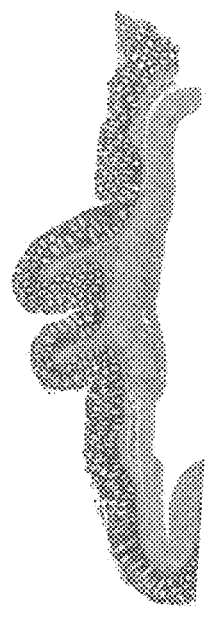
FIG. 6

METHOD AND COMPOSITION FOR TREATING INFLAMMATORY BOWEL DISEASE

BACKGROUND

Inflammatory Bowel Disease (IBD) consists of two independent diseases: Crohn's Disease (CD) and Ulcerative Colitis (UC), affecting 833,000 Americans.

While CD can manifest anywhere along the digestive tract (mouth to anus) and often affects the entire thickness of the digestive tract wall, UC is confined to the colon and rectum and affects only the mucosa (inner lining) of the wall.

Medical treatments, including use of anti-inflammatories that may have severe side effects, may fail in treating the symptoms of UC, and complete removal of the colon (colectomy) is the only known "cure" for UC when the patient is refractory to all other medical treatments. Colectomy is a well-established but major surgery, often requiring an ileostomy to facilitate waste removal.

Alternatives to first lines of treatment (medications with potentially harmful side effects) and second lines of treatment (colectomy) are needed for treating and curing IBD, including UC.

The trend toward minimally invasive surgical procedures has prompted the development of artificial scaffolds useful for tissue regeneration. Purified collagen, gelatin, autologous fat, hyaluronic acid, and synthetic materials have been clinically used as injectable scaffolds in regenerative medicine for the treatment of urinary incontinence, reflux disease, laryngeal pathologies, and neonatal cardiomyocytes. However, overly-purified, chemically modified or synthetic materials can lead to adverse immune responses by the host and limit cell migration into the matrix.

Naturally occurring extracellular matrix (ECM)-derived scaffolds possess many bioactive properties and have been used for the repair of a variety of tissues, including lower urinary tract structures, esophagus, cardiac tissue, and musculotendonous structures. However, many of these scaffolds are derived from non-human tissue, and none have been described for use in the treatment or regeneration of lower intestine tissue, such as colon tissue, and not specifically for the treatment of UC.

SUMMARY OF THE INVENTION

The subject invention concerns a novel tissue graft and method for treating UC by replacing diseased or damaged mucosal tissue without colectomy.

In one embodiment, a method of the invention comprises treating damaged or diseased lower intestinal tissue by the steps of (1) optionally performing a mucosectomy on the diseased or damaged mucosal lining of the colon, and (2) seeding the mucosal lining of the colon with stem or progenitor cells, or stimulating stem and progenitor cell migration to the diseased or damaged colon tissue in a patient having symptoms of, or suffering from, disease or damage to the mucosal lining of the colon. A disease of the mucosal lining of the colon can be Inflammatory Bowel Disease (IBD), and the method can be used to treat, ameliorate, or cure IBD.

Thus, the subject invention can comprise seeding of stem cells or progenitor cells by delivery of the stem cells or progenitor cells directly to the damaged or diseased colon tissue, e.g., wherein the stem cells or progenitor cells are prepared in a fluid composition, such as a solution, suspension, or gel, for delivery to the colon tissue by injection or infusion into the lumen of the colon so that the stem cells or progenitor cells contact, and at least temporarily reside on, the luminal wall of the colon in order to initiate or stimulate reconstructive tissue remodeling of the mucosal lining of the colon. Thus the method of the invention can effect replacement of damaged or diseased colon tissue with new, healthy colon tissue.

Alternatively, stem cells or progenitor cells can be stimulated to the site of the damaged or diseased colon tissue by introducing onto, or in contact with, the colon luminal wall an extracellular matrix (ECM) composition, e.g., an ECM graft or scaffold, in the form of a solid (sheet or tube) or fluid (solution, suspension, or gel).

In another embodiment of the invention, stem cells or progenitor cells can be incorporated into the solid or fluid ECM composition, and the ECM composition comprising stem cells or progenitor cells can be delivered to the mucosal lining of the colon by delivery means appropriate for the composition as described herein. For example, a solid ECM can be endoscopically implanted onto the colon lining, or a fluid ECM can be infused, injected, or sprayed into the colon.

Once seeded or migrated to the site of damaged colon tissue, the stem cells or progenitor cells specialize, develop in situ, and replace the mucosal lining of the colon. The method can further include one or more of the additional steps of: (3) creating an ileostomy, and (4) providing Total Parenteral Nutrition (TPN) to the patient by feeding the patient intravenously, bypassing the digestive tract while the new mucosa forms and replaces the diseased mucosal lining.

When employed as part of the method of the invention, the mucosectomy step, which removes the diseased or damaged tissue prior to implantation, transplantation, or administration of the graft, can be carried out by tissue resection or ablation.

Resection or ablation methods include endoscopic or surgical mucosal resection (excision), endoscopic laser therapy, photodynamic therapy, endoscopic thermocoagulation using argon plasma coagulation, radiofrequency ablation, cryoablation, or the use of EDTA or other ablating agent. These mucosectomy procedures are well documented in the art. Any one or more of the above techniques or procedures may be used in a method of the subject invention where a resection or ablation step is employed.

The subject invention further includes a method and composition for treatment of disease- or trauma-damaged tissue using a tissue graft, such as an extracellular matrix (ECM) scaffold, derived from the same tissue being treated. A tissue graft comprising ECM derived from the same tissue as the tissue being treated, is referred to herein as a "tissue-specific extracellular matrix" (TS-ECM).

A preferred TS-ECM is derived from not only the same type of tissue (i.e., colon-derived ECM for colon tissue treatment), but is also derived from the same species as the species being treated. For example, treatment of UC in a human will employ human colon mucosal tissue as the TS-ECM scaffold composition. The tissue graft can be an allograft or xenograft. Reciprocal exchange of stimuli and information (known and referred to in the art as "dynamic reciprocity") can exist between ECM and cells, providing an advantage for using ECM grafts. This dynamic reciprocity can be facilitated or improved by the use of TS-ECM grafts.

Thus, the subject invention includes, but is not limited to, a tissue graft composition derived from large intestine tissue for replacement of diseased or damaged large intestine tissue. The ECM derived from large intestine tissue can preferably comprise colon mucosa, and the treated large intestine or colon tissue can preferably be colon mucosa.

In one embodiment, the tissue graft composition can be an ECM scaffold formed as a solid sheet or tube which can be placed or secured onto the colon mucosa. A solid sheet or tube scaffold can be implanted or transplanted or, as recognized in the art, affixed, applied, or attached, at a desired site in a patient by mechanical or surgical means, including but not limited to sutures, staples, stents, or clips, or can be adhered to the mucosa by an acceptable adhesive, such as a pharmaceutically acceptable or therapeutically acceptable adhesive, including a bioadhesive. One preferred procedure for delivering an ECM composition to the colon can employ an endoscope, which can advantageously minimize invasive surgical procedures.

Alternatively, the ECM can be powdered or digested, and solubilized or suspended for presentation in the form of a fluid, such as a gel, solution, or suspension. A fluid composition can advantageously be administered by injecting, infusing, spraying, or the like, the gel, solution or suspension to the site being treated. For example, a fluidized ECM can be administered or applied by being injected, infused, or sprayed into the lumen of the colon, e.g., as an enema therapy whereby the fluid ECM coats the mucosal lining of the colon or, in the case of mucosectomized colon, coats the exposed lumen wall of the colon. Such administration can be repeated several times, including one or more times a day for a period of several days, weeks or months, up to about one year as determined by the treating physician monitoring for acceptable regrowth or replacement of viable or healthy tissue, as desired.

One preferred embodiment of a sprayable gel, solution or suspension of a fluidized ECM is to aerosolize the composition for administration by spraying. The aerosolized spray can be pumped from a source reservoir, through a cannula or other conduit provided in or with an endoscope manufactured or modified to deliver such fluidized ECM to the desired site or location.

Advantageously, stem cells or progenitor cells are known to migrate to the site of the ECM placement or administration and, over time, can replace the tissue with healthy or non-symptomatic cells and tissue having the normal properties and function of those cells or tissue. Thus, alternative embodiments of a composition of the invention include a solid ECM tube or sheet scaffold, alone; a solid ECM scaffold coated or embedded with stem or progenitor cells; a fluidized ECM (e.g., gel), alone; or a solid ECM scaffold additionally comprising fluidized ECM, with or without stem or progenitor cells coated, embedded, or mixed with the solid or fluid ECM.

It would also be understood that the ECM composition can be a hybrid, being derived in part from natural tissue and mixed or combined with a synthetic or natural polymer. It is preferable, but not required that a biodegradable polymer be used in an ECM composition of the invention comprising a synthetic or natural polymer.

In another embodiment of the invention, e.g., a solid sheet or tube ECM composition, can be formed or produced by use of three-dimensional (3-D) printer technology.

The composition can further include an additive for effecting a particular desired property to the ECM. For example, the ECM composition can include one or more drugs or biologics, such as an antibiotic, anti-inflammatory, immunosuppressant, monoclonal antibody, growth factor, or the like, providing a desired activity of the added drug or biologic. These additives can make the local environment conducive to favorable tissue remodeling. Other additives to the composition can include, for example a viscosity enhancing agent, or an agent which can initiate or retard the formation of gel. It is generally accepted in the art that higher viscosity of a gel can provide improved adhesion and tenacity properties of the gel. Accordingly, a viscosity enhancing agent can also serve to facilitate adhesion to the target tissue. Adhesive facilitators are well known in the art, but can further include blood components, such as blood coagulants or blood coagulation factors, as a viscosity enhancing agent or adhesion enhancing agent.

Also included as part of the invention is a method for treating diseased or damaged colon tissue using an ECM graft or scaffold as described herein, without prior resection or ablation. For example, in instances where disease or damage to the tissue creates a lesion or tissue insult, such as an exposed or bleeding surface of the tissue, resection of the tissue prior to implantation, transplantation, application, or administration of the ECM scaffold or graft composition may be omitted. Accordingly, one embodiment of the subject method comprises the steps of:

a) preparation of an ECM scaffold, graft, or composition using tissue selected from intestine, reproductive, integumentary, pancreatic, renal, circulatory, and respiratory, and b) implanting, transplanting, applying or administering the ECM graft or scaffold composition onto tissue in a patient suffering from a disease or condition affecting the lower intestinal tract tissue in a patient suffering from disease, damage, or a condition affecting the intestinal tissue, wherein the intestinal tissue is not subjected to resection or ablation prior to the implantation, transplantation, application or administration of the ECM composition.

In a preferred embodiment, this method comprises treating damaged or diseased colon tissue exhibiting IBD, such as Ulcerative Colitis or Crohn's Disease; familial adenomatous polyposis; Hirschsprungs; stricture; proctitits; colon cancers; rectal mucositis or fistula, and more preferably, treating disease or damage to colon mucosa tissue.

Another embodiment of the invention is a method for treating diseased or damaged tissue using a tissue-specific ECM (TS-ECM) scaffold as described herein, with or without prior resection or ablation. Accordingly, one embodiment of the subject method comprises the steps of:

a. optionally performing a mucosectomy on the damaged or diseased tissue;

b. preparing a TS-ECM graft or scaffold composition using tissue selected from intestine, reproductive (other than vaginal), integumentary, pancreatic, renal, circulatory, and respiratory, and c. implanting, transplanting, or administering the TS-ECM scaffold or composition onto tissue in a patient suffering from a disease or condition affecting the same intestinal, reproductive (other than vaginal), integumentary, pancreatic, renal, circulatory, and respiratory tissue.

It would be understood that an ECM or TS-ECM graft, scaffold or composition of the invention can be a biocompatible porous, macroporous, or microporous matrix wherein stem cells or ECM gel, solution or suspension can be dispersed. In addition, an ECM or TS-ECM of the invention can be gelled.

Methods for preparing tube, sheet, and gelled, solubilized ECM compositions, useful as cell growth matrices or scaffolds used as grafts, are described in the art. Gel ECM compositions can be molded prior to implantation or administered to a patient in an un-gelled form prior to gelation where the composition gels in situ. These, and other methods of forming ECM grafts are described in, for example, U.S. Pat. No. 8,361,503, which is incorporated by reference in its entirety.

In a preferred embodiment, a gel ECM composition is prepared according to one or more processes as described. For example, a gel ECM can be prepared by a method comprising:

i) comminuting an ECM in solid form, ii) solubilizing intact, non-dialyzed or non-cross-linked ECM by digestion with an acid protease in an acidic solution to produce a digest solution, iii) adjusting the pH of the digest solution to a pH between 7.2 and 7.8 to produce a neutralized digest solution, and iv) gelling the solution at a temperature greater than 25° C.

In one embodiment, the preparation of the ECM composition can include further processing of the solubilized ECM produced by step (ii), wherein the solubilized ECM is dried or lyophilized to form a dry powder which can be stored for a longer period of time than a solubilized ECM in liquid form. The dry powder ECM can then be reconstituted in an aqueous solution or buffer and brought to neutral pH as in step (iii), above.

In another embodiment the method of preparing an ECM graft or scaffold composition further includes ultrasonicating the scaffold. A further method of the invention comprises attaching a TS-ECM scaffold to tissue of a patient wherein the surface of the scaffold comprises a gelled solubilized ECM embedded or coated with a patient's cells, e.g., stem cells, wherein the embedded or coated cells are allowed sufficient time for in-growth of the patient's cells into the scaffold prior to implanting, transplanting, or administering the scaffold to the tissue.

In carrying out a method of the invention, a scaffold or graft is prepared as described herein, or other known method of preparing ECM, then implanted, transplanted, or administered to at least a section of tissue which is diseased or damaged, and allowed to remain in contact with the diseased or damaged tissue for a sufficient period of time so that replacement cells grow and replace the diseased or damaged cells. A sufficient period of time can be from one day to about six months.

Advantageously, the implantation, transplantation, or administration of an ECM graft provides a stimulus for migration of stem cells to the site of implantation, transplantation or administration of the ECM graft. For example, in treating UC, an ECM graft is implanted, transplanted or administered in contact with at least a section of the colon where the diseased or damaged colon mucosa was (in the case of post-mucosectomy) or is (in the case where mucosectomy is not preformed), retained in contact with the mucosa for a period of time to allow growth and replacement of colon mucosal cells, resulting in replacement of the diseased or damaged cells with healthy cells. The ECM graft can be provided as a relatively short solid segment, on the order of 1-10 centimeters, concomitantly or sequentially implanted, transplanted or administered to the inner wall of the colon. Alternatively, the ECM graft can be prepared having a plurality of sections or lengths corresponding to the entire colon.

Extracellular Matrix (ECM), or Extracellular Matrix Hydrogel (ECMH, i.e. ECM in liquid or fluid, gellable form) can also be useful in the treatment or prevention of diseases or conditions that are not autoimmune related, such as rectal mucositis, which can present in patients undergoing radiation or chemotherapy. For example, ECMH therapy, e.g., administering ECMH by enema before radiation or chemotherapy treatments are initiated, and continuing ECMH administration throughout the course of such radiation or chemotherapy can prevent the onset of rectal mucositis in the patient.

It would be understood that the ECMH administration can be carried out using different administration regimens which are dependent on the need of the patient and a determination by the physician or other caregiver. For example, the ECMH administration can be initiated after the radiation or chemotherapy begins, wherein the physician or caregiver can monitor the need for ECMH administration and evaluate the condition of the rectal mucosa for need of such ECMH therapy.

The dosing regimen for administering the ECMH can also depend on need and condition of the patient. For example, the patient can receive ECMH administration one or more times per day, e.g., up to four times per day, or can receive daily enemas using ECMH. Alternatively, the patient can receive ECMH administrations one to five times per week, preferably three to five times per week, every other day or every third day. The therapy or dosing regimen can be provided to a patient for up to about 8-12 weeks, or longer as determined by the attending physician or specialist.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3 shows Tables of the criteria determinations for the rat study described in Example 3: Table 1 shows the criteria for clinical symptoms scoring; Table 2 shows the criteria for gross anatomical scoring of colon specimens; and Table 3 shows criteria for histologic scoring of colon specimens.

FIG. 4A is a graph of weight loss/per day; FIG. 4B is graph of stool blood score per day; FIG. 3C is a graph of stool consistency per day; FIG. 4D is a graph of colon length of DSS-treated versus non-DSS treated rats; and FIG. 4E is a graph of TRITC concentration for DSS-treated versus non-DSS-treated rats.

FIGS. 5A-5D show inflammation scores for distal and proximal colon sections in ECMH-treated rats versus vehicle-treated sham control rats or healthy rats; FIGS. 5E-5H show ulceration scores for distal and proximal colon sections in ECMH-treated rats versus vehicle-treated sham control rats or healthy rats.

FIG. 6 shows tissue regeneration of colonic mucosa, illustrating ulceration and inflammation in colons from ECMH-treated rats versus vehicle sham control or healthy rats.

FIG. 7A shows weight score per day; FIG. 7B shows stool blood score per day; FIG. 7C shows stool consistency score per day; FIG. 7D shows colon length in ECMH-treated rats versus vehicle-treated sham and healthy rats' colons; and FIG. 7E shows a graph of the gross score of disease state in ECMH-treated rat colon versus vehicle-treated sham rat colon.

FIG. 11A shows lamina propria mononuclear cells (LPMC) secreted TNFα concentrations in ECMH-treated versus vehicle-treated and NT (not treated); FIG. 11B shows LPMC secreted PGE2 concentrations in ECMH-treated versus vehicle-treated and NT; and FIG. 11C shows secreted PGE2 levels from organotypic cultures from rat colons treated with ECMH-treated versus vehicle-treated and healthy rats.

FIG. 12 shows, graphically and photographically, mucoadhesion of ECMH, wherein: FIG. 12A is a graph of tensile adhesion strength in pepsin-treated rat colon versus 4 mg/ml, 8 mg/ml, and 12 mg/ml concentrations of ECMH; FIG. 12B shows a graph of tensile strength in healthy versus diseased rat colon; FIG. 12C shows percent ECMH remaining at 2 hrs, 12 hrs., and 24 hrs. following administration of $^{14}C$-labeled ECMH; FIG. 12D is a photographic representation of FITC-labeled ECMH present in the colon at 1 hr., 2 hr., 12 hr., and 24 hours following administration of ECMH.

FIG. 13A is a graphic representation of TRITC concentration in ECMH-treated rats versus vehicle-treated sham rats and healthy rats; FIG. 13B is a graphic representation of relative change in TEER in ECMH-treated cell culture versus LPS+ECMH-treated cell culture, LPS-only treated cell culture, and NT cell cultures; FIG. 13C is a graphic representation of percent E-cad cells in LPS+ECMH-treated rats versus LPS-only treated rats, and NT rats; and FIG. 13D shows a photographic representation of cells in healthy versus LPS-damaged, versus LPS+ECMH treated cell cultures.

DETAILED DESCRIPTION OF THE INVENTION

Figure 1:
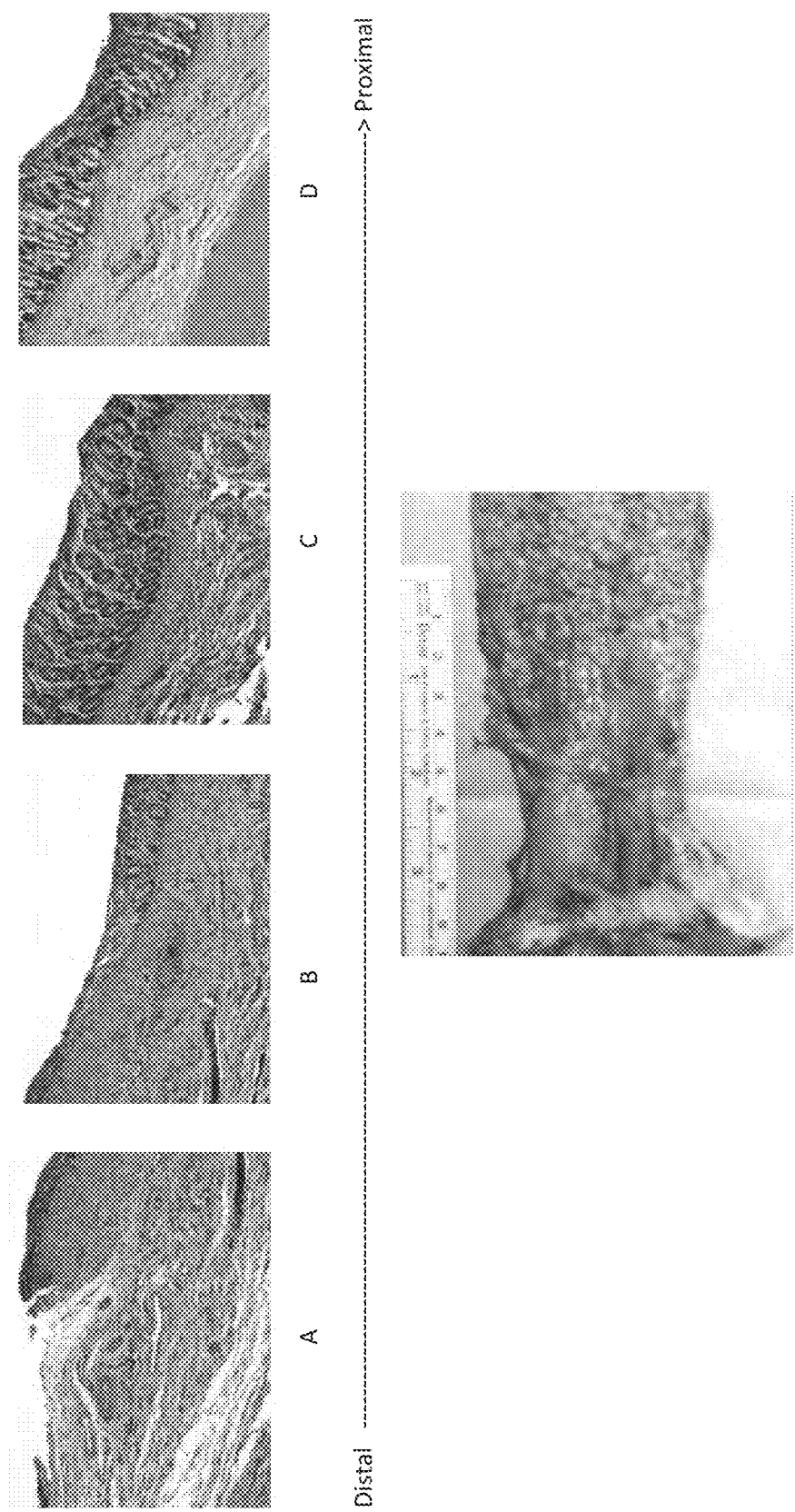
FIG. 1 shows the results of a colon section (lower photograph) removed from a dog treated with Small Intestinal Submucosa Extracellular Matrix (SIS-ECM) as described herein; micrographs (upper photographs A-D) show microscopic cellular examinations along the distal 4 proximal gradient of the colon section illustrating an increased mucosal coverage along the gradient, namely, incomplete mucosal coverage is seen at the distal anastomosis (A), and increasing mucosal coverage is present toward the proximal ends (B), (C), and (D).
Figure 2:
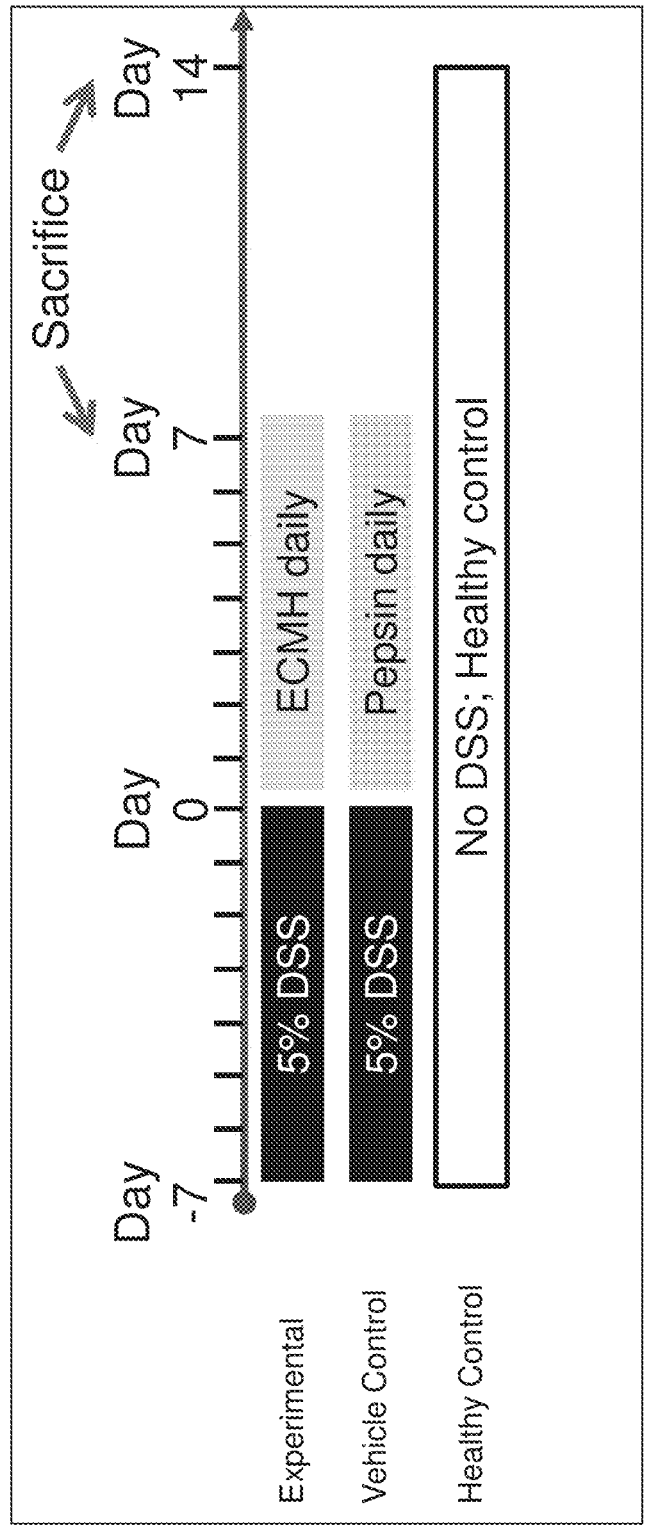
FIG. 2 shows a schematic of the rat study design and measurements as described in Example 3.

The subject invention concerns treating Inflammatory Bowel Disease (IBD), for example Ulcerative Colitis (UC) or Crohn's Disease (CD), or the like, by replacing or stimulating replacement of diseased or damaged mucosal cells and tissue without colectomy.

In one embodiment, a method of the invention comprises treating damaged or diseased lower intestinal tissue by the steps of (1) optionally performing a mucosectomy on the diseased or damaged mucosal lining of the colon, and (2) seeding the mucosal lining of the colon with stem or progenitor cells, or stimulating stem and progenitor cell migration to the diseased or damaged colon tissue in a patient having symptoms of, or suffering from, disease or damage to the mucosal lining of the colon. A disease of the mucosal lining of the colon can be Inflammatory Bowel Disease (IBD), and the method can be used to treat, ameliorate, or cure IBD.

Thus, the subject invention can comprise seeding of stem cells or progenitor cells by delivery of the stem cells or progenitor cells directly to the damaged or diseased colon tissue, e.g., wherein the stem cells or progenitor cells are prepared in a fluid composition, such as a solution, suspension, or gel, for delivery to the colon tissue by injection or infusion into the lumen of the colon so that the stem cells or progenitor cells contact, and at least temporarily reside on, the luminal wall of the colon in order to initiate or stimulate reconstructive tissue remodeling of the mucosal lining of the colon. Thus the method of the invention can effect replacement of damaged or diseased colon tissue with new, healthy colon tissue.

Alternatively, stem cells or progenitor cells can be stimulated to the site of the damaged or diseased colon tissue by introducing onto, or in contact with, the colon luminal wall an extracellular matrix (ECM) composition, e.g., an ECM graft or scaffold, in the form of a solid (sheet or tube) or fluid (solution, suspension, or gel).

In another embodiment of the invention, stem cells or progenitor cells can be incorporated into the solid or fluid ECM composition, and the ECM composition comprising stem cells or progenitor cells can be delivered to the mucosal lining of the colon by delivery means appropriate for the composition as described herein. For example, a solid ECM can be endoscopically implanted onto the colon lining, or a fluid ECM can be infused, injected, or sprayed into the colon.

By design, ECM breaks down rapidly in situ and can encourage an inflammatory response, including migration of macrophages to the site. One unique characteristic of ECM is to encourage a switch in the phenotype of these macrophages from type M1 (pro-inflammatory, such as would be seen in a patient suffering from UC) to type M2 (pro-tissue remodeling, such as would be seen in a person without an underlying pro-inflammatory condition). An important ramification of this M1 to M2 phenotype switch is to allow tissue that is otherwise predisposed to inflammation to remain healthy.

The optional mucosectomy step, which is carried out to remove diseased or damaged tissue, e.g., colon mucosal tissue, prior to implantation, transplantation, or administration of a graft, can be performed using any commonly accepted method, such as tissue resection or ablation. Known resection or ablation methods include endoscopic or surgical mucosal resection (excision), endoscopic laser therapy, photodynamic therapy, endoscopic thermocoagulation using argon plasma coagulation, cryotherapy, radiofrequency ablation or ablation using EDTA or other ablating agent.

Seeding the mucosectomized tissue with stem or progenitor cells can be carried out by known methods, such as injection of stem cells at the site, as described in the medical literature. See, for example, Lanzoni, G., *Inflammatory bowel disease*: Moving toward a stem cell-based therapy, World J Gastroenterol. 14(29): 4616-4626 (Aug. 7, 2008), which summarizes the use of hematopoietic and mesenchymal stem cells in treating IBD, but does not teach or suggest prior mucosectomy.

Preferably, stem cells can be introduced to a mucosectomized tissue by placing and/or securing, e.g., implanting, transplanting, or administering, extracellular matrix (ECM)

material or composition as an ECM scaffold or graft at the site. Introduction of an ECM composition to the mucosectomized site can be in the form of a solid sheet or tube, or can be in the form of a fluid, such as a solution, suspension or gel. The placement or securing of the solid ECM material can be by sutures, clips, staples, glue, or other securing means as is well known.

Alternatively, a fluidized ECM can be administered by a commonly employed fluid administration or delivery process such as injection, infusion or drench ("squirting" onto the site) or by spraying the fluid onto the site. A preferred spraying technique is carried out using an aerosolized ECM fluid, delivered, for example endoscopically.

As used herein, the terms "composition," "material," "scaffold," and "graft," as referring to ECM, can be used interchangeably, and do not connote a particular configuration, such as being in solid, liquid, fluid or other form. For example, an "ECM scaffold" can be solid or fluid.

Preferably, a fluidized ECM composition is formed as a gel such that it has viscous properties, and has a viscosity sufficient so that the fluid is self-adhering to the desired location within the body. In a preferred embodiment, the fluidized ECM is a hydrogel having relatively non-viscous liquid properties when applied or administered, which advantageously thickens or becomes more viscous, forming an adhesive gel upon, or shortly following, contact with the body at the site of administration or application. Gelation can be initiated by increased temperature, such as body heat, following administration. The fluid ECM can also be mixed with a separate viscous agent, such as a hydrogel or other commonly known gelling agent, to provide sufficient viscosity. Alternatively, two fluids can be administered whereby at least one of the fluid contains ECM material, and wherein the two fluids gel when coming into contact with one another or when mixed.

It is well established that an ECM composition can cause stem cells to migrate to the site when sufficient vascularization of the tissue exists, and the blood vessels provide an adequate conduit for the cells to migrate to the site. In addition, ECM communicates with the adjacent or underlying tissue via chemical signaling, and the adjacent or underlying tissue communicates with the ECM, by a phenomenon termed "dynamic reciprocity" which optimizes cell and tissue replacement or regeneration where ECM is used. Thus, the ECM composition can serve as a solid, liquid or gel scaffold for new cellular and tissue growth at the site of placement, administration, or application.

In a further embodiment, an ECM-derived composition can be a tissue graft whereby the ECM composition serves as a scaffold for promoting new growth of tissue at the site of implant. The scaffold can be an ECM tube or sheet placed at the desired site. The scaffold can be a biocompatible porous, macroporous, or microporous matrix, wherein stem cells or ECM gel, solution or suspension can be dispersed. The ECM can also be subsequently gelled following dispersion of the stem cells or ECM solution or suspension.

In one embodiment, an ECM can be derived from tissue commonly used in the art. For example, ECM has been derived from small intestinal submucosa (SIS) or urinary bladder matrix (UBM) tissue. One preferred embodiment using UBM is UBM tissue without the epithelial basement membrane layer.

In a more preferred embodiment, it has been discovered that ECM derived from the same tissue type as the tissue being treated, referred to as "tissue-specific extracellular matrix" or "TS-ECM," can provide advantageous results, such as more efficient or more responsive reconstructive tissue remodeling, which can occur through dynamic reciprocity.

Thus, the subject invention further includes a method and composition for treatment of disease- or trauma-damaged lower intestinal tract, reproductive (other than vaginal), integumentary, pancreatic, renal, circulatory, or respiratory tissue, using a TS-ECM graft. In one embodiment, TS-ECM is derived from the same species as the species being treated. For example, treatment of UC in a human will employ human colon mucosal tissue as the TS-ECM scaffold composition. The tissue graft can be an autograft, allograft, as described above, or xenograft.

In one preferred embodiment, the subject invention includes a method of use, and a composition comprising, a tissue graft composition derived from large intestine tissue for replacement of diseased or damaged large intestine tissue. The derived large intestine tissue or the treated large intestine tissue can be colon tissue, and can preferably be colon mucosa.

Advantageously, in tissue disease, damage or conditions that cause open or bleeding lesions, such as exhibited by colon tissue in patients suffering from IBD, such as CD or UC, it is contemplated that a treatment or cure can be effected by a method comprising implantation, transplantation or administration of the TS-ECM without a prior step of mucosal resection or ablation. Thus, in such instances where disease or damage to the tissue creates a lesion, such as an exposed or bleeding surface of the tissue, resection of the tissue prior to may be omitted.

As used herein, the terms implanting or implantation, transplanting or transplantation, applying or application, administering or administration, infusing or infusion, injecting or injection, delivering or delivery, all refer to the process or providing an ECM to the site of treatment, and would be understood by a person of ordinary skill in the art to have the same meaning, depending on the composition properties and procedure employed for carrying out the delivery of ECM to the site. These terms can be used interchangeably and are in no way limiting to the method of the invention.

Accordingly, one embodiment of the subject method comprises the steps of:

preparation of a TS-ECM scaffold using tissue selected from lower intestinal tract, reproductive (other than vaginal), integumentary, pancreatic, renal, circulatory, and respiratory, and implanting, transplanting, or administering the TS-ECM scaffold onto tissue in a patient suffering from a disease or condition affecting the same lower intestinal tract, reproductive (other than vaginal), integumentary, pancreatic, renal, lower intestinal tract, circulatory, and respiratory tissue.

Optionally, when treating the colon, the method can further include one or more of the additional steps: (3) creating an ileostomy, and (4) providing Total Parenteral Nutrition (TPN) to the patient by feeding the patient intravenously while the new mucosa forms.

In a preferred embodiment, this method comprises treating damaged or diseased colon tissue. The method can be employed, for example, to treat damage to or disease of colon tissue resulting from Crohn's Disease, Ulcerative Colitis, familial adenomatous polyposis, Hirschsprungs, stricture, proctitis, rectal mucositis, or fistula, and more preferably, treating disease or damage to colon mucosa tissue.

Methods for preparing tube, sheet, and gelled, solubilized ECM compositions, useful as cell growth scaffolds, are described in the art. Gel ECM compositions can be molded prior to implantation or administered to a patient in an un-gelled form prior to gelation where the composition gels in situ.

These, and other methods of forming ECM grafts are described in, for example, U.S. Pat. No. 8,361,503, which is incorporated by reference in its entirety. In a preferred embodiment, a gel ECM composition is prepared according to one or more processes as described. For example, a gel ECM can be prepared by a method comprising:

i. comminuting an ECM,
  ii. solubilizing intact, non-dialyzed or non-cross-linked ECM by digestion with an acid protease in an acidic solution to produce a digest solution,
  iii. adjusting the pH of the digest solution to a pH between 7.2 and 7.8 to produce a neutralized digest solution, and
  iv. gelling the solution at a temperature greater than 25° C.

In another embodiment the method of preparing an ECM scaffold further includes ultrasonicating the scaffold. In yet another embodiment, following solubilizing of the comminuted ECM in step (ii), the solubilized ECM can be dried to powder form. Drying can be achieved by lyophilization or another drying process known in the art. This drying step can advantageously provide longer storage time for the composition compared to storage in liquid, solubilized form. When ready for use, the dried powder form can be reconstituted with an aqueous solution or buffer and the process of pH adjustment (e.g., neutralization of pH) can be carried out in step (iii) and the process continued. Alternatively, the pH adjustment of step (iii) can be carried out before the drying process.

A further method of the invention comprises attaching a TS-ECM scaffold to tissue of a patient wherein the surface of the scaffold comprises a gelled solubilized ECM embedded or coated with a patient's cells, e.g., stem cells, wherein the embedded or coated cells are allowed sufficient time for in-growth of the patient's cells into the scaffold prior to implanting, transplanting, or administering the scaffold to the tissue.

In carrying out a method of the invention, a scaffold graft is prepared in accordance with the description herein, then implanted, transplanted, or administered to at least a section of tissue which is diseased or damaged, and allowed to remain in contact with the diseased or damaged tissue for a sufficient period of time so that replacement cells grow and replace the diseased or damaged cells.

A sufficient period of time can be from one day to a few weeks or months, depending on the responsiveness of the patient to such treatment method. A one-year period of treatment without successful tissue reconstruction may be an upper limit for continuing such treatment. The ECM material biodegrades naturally in the body and is not required to be removed. Nevertheless, ECMH unexpectedly and advantageously provides a barrier layer over the lesion to be treated. This property is unexpected because one or more of the viscosity or tenacity or adhesion characteristic of the liquid form and resultant gel was found to be resistant to elimination from intestine, even with the peristaltic movement or motility within the intestine of the patient being treated, or ingested liquids moving through the intestine.

Thus, ECMH forms a barrier layer or protective layer during its residence within the intestine. The residence time for the ECMH is long enough to provide efficacious tissue healing and repair, and is on the order of at least two hours, up to 48 hours. Preferably, the residence time of ECMH following administration is about four to about 24 hours, and more preferably from about six hours to about 12 hours.

For carrying out the subject method treating UC, an ECM graft is implanted, transplanted or administered in contact with at least a section of diseased or damaged colon, retained in contact with the mucosa for a period of time to allow growth and replacement of colon mucosal cells, resulting in replacement of the diseased or damaged cells with healthy mucosal cells that do not exhibit inflammation or other manifestations of UC-diseased cells.

The ECM graft can be provided as a relatively short tube or sheet segment, on the order of 1-10 centimeters in length, implanted, transplanted or administered to the inner wall of the colon. Alternatively, the ECM graft can comprise one or more lengths which correspond to the entire length of the colon. A solid tube or sheet ECM can be secured to the tissue to be treated by suturing, clips, staples, glue, or the like. Alternatively, the colon tissue can be treated by administering, e.g., spraying, a liquid solution, suspension, or gel composition onto the site being treated.

In a method of treating UC that includes a mucosectomy step, the tissue exhibiting the symptoms of UC is removed, since UC is confined within the mucosa. The mucosectomy step can be performed endoscopically, obviating the need for open or laparoscopic surgery. The stem cell stimulation step (via introduction of TS-ECM graft) allows a new, healthy mucosa to form in the colon lumen. The mucosectomy can be done to a partial or short segment of the colon or longer lengths of the colon.

Whether carried out on a segment of the colon or the entire length of the colon, the subject invention can offer benefits which eliminate the need for colectomy and leaving a native rectal tissue cuff, in situ, including the benefits of removing the malignant potential in the retained rectum from proliferative (malignant) pathologies, e.g., UC or familial polyposis; and allowing a healthcare professional to leave a longer rectosigmoid segment in place, with functional benefits of:

Decreased risk of sphincter disruption (incontinence) or sacral nerve damage (impotence) that come with lower dissections, and Improved reservoir function, allowing more normal bowel habits because of increased water absorption and improved storage capacity;

Offers relative simplicity and less invasiveness than colectomy or similar procedures such as IPAA (total proctocolectomy with ileoanal anastomosis); a mucosectomy is a fairly straightforward procedure which can be done from below at same time as the pull-through/ileostomy or at any time later. The stem cells could be "planted" and regenerate the mucosa while the diverting ileostomy is still extant.

Sparing the colon obviates the lifelong concerns of living without a colon (e.g. pouchitis, intestinal blockage, dehydration, sleep deprivation due to the need for frequent bowel movements resulting from decreased rectal reservoir capacity, etc.);

Creates only a temporary Ileostomy (i.e., until the new mucosa is viable); and

It brings together various disciplines (surgical, medical, endoscopic, and tissue engineering) that might otherwise work independently to treat IBD.

It would be understood that various methods and procedures can be used to deliver stem cells to the colon, e.g. on a scaffold, in a broth delivered via enema, by a catheter-based delivery system, or the like. Advantageously, the ECM material can be applied during the same surgical procedure as when the ileostomy is created, and the mucosa can be allowed to proliferate or regenerate while the internal pouch heals.

EXAMPLE 1

Surgical Placement of Solid ECM for Replacement of Colon Tissue

Small intestine submucosal extracellular matrix (SIS-ECM) grafts were grafted into the colon tissue of four (4) living dogs. The SIS-ECM grafts of approximately 3-4 centimeter lengths were prepared in accordance with known techniques. Grafts were prepared having different numbers of layers—2-layer, 4-layer, 6-layer, and 8-layer sheets or tubes and tested following transanal circumferential mucosal resection.

Four (4) healthy adult mongrel female dogs (approx. 20 kg in weight) were subjected to circumferential colon mucosal EMR. With the dog under general anesthesia, surgical mucosectomy was performed. Alternatively, mucosal tissue ablation, such as EMR can be performed, e.g., with a therapeutic endoscope (EG-3430, Pentax Medical, Montvale, N.J.) and a commercially available kit (EMR Kit, Olympus America, Center Valley, Pa.). Piecemeal mucosal resections were sequentially performed until a 4-cm circumferential resection was completed.

A tubular ECM graft or scaffold derived from the porcine small intestine submucosa (SIS) was then endoscopically surgically placed in the four dogs. The SIS-ECM biologic scaffold material was prepared as previously described and configured into a tubular shape. In brief, porcine SIS was harvested from market-weight pigs (approximately 110-130 kg) immediately after death. Residual external connective tissues, including adipose tissue, were trimmed and all residual waste material was removed by repeated washes with tap water. The submucosal layer was mechanically delaminated from the small intestine tissue. The submucosal layer was then decellularized and disinfected by immersion in 0.1% (vol/vol) peracetic acid (s), 4% (vol/vol) ethanol, and 96% (vol/vol) deionized water for 2 hours.

The SIS-ECM material was then washed twice for 15 minutes with phosphate-buffered saline solution (pH 7.4) and twice for 15 minutes with deionized water. Tubular scaffolds were fabricated to match the anatomy of the canine colon. Briefly, multilayer tubes were created by wrapping hydrated sheets of SIS around a 22-mm perforated tube/mandrel that was covered with umbilical tape for a total of several complete revolutions (i.e., a multi-layer tube). The constructs were then placed into plastic pouches and attached to a vacuum pump (model D4B, Leybold, Export, Pa.) with a condensate trap in line.

The constructs were subjected to a vacuum of 710 to 740 mm Hg for 10 to 12 hours to remove the water and form a tightly coupled multi-laminate construct. After each ECM device was removed from the mandrel, they were terminally sterilized with ethylene oxide.

For endoscopic placement of the SIS-ECM graft, the tubular scaffold was hydrated in a saline solution bath for 5 minutes and then placed over a 30-mm achalasia balloon (Cook Endoscopy Achalasia balloon, Wilson-Cook Medical, Winston-Salem, N.C.). The SIS-ECM device was constrained with two 4-0 silk sutures with surgeon's knots that would release when the balloon was inflated. A 0.035-inch wire (Jagwire, Boston Scientific, Natick, Mass.) was endoscopically placed into the dog's colon. The balloon was then passed over the wire and positioned under endoscopic guidance with the SIS-ECM bridging the length of the mucosal resection.

One ml of a degradable, lysine-derived urethane (LDU) surgical adhesive (TissuGlu, Cohera Medical, Pittsburgh, Pa.) was then injected through a 6F endoscopic guiding catheter (Oasis stent introduction system, Wilson-Cook Medical) between the colon wall and the SIS-ECM in 2 separate strips on opposite sides of the device to prevent slippage. The balloon was then manually inflated to full capacity, expanding the scaffold against the colon wall. Balloon inflation was maintained for 15 minutes before deflation and removal, leaving the SIS-ECM scaffold in place within the colon.

Postoperatively, the dogs were recovered from anesthesia, extubated, and monitored in the recovery room until they were resting comfortably in a sternal position. The dogs were kept in a cage overnight and returned to their larger run housing on postoperative day 1. All dogs were given oral prophylactic antibiotics consisting of cephalothin/cephalexin (35 mg/kg) twice daily for 7 to 9 days.

Intravenous acepromazine (0.1 mg/kg) and butorphanol (0.05 mg/kg) were administered for 2 days, followed by subcutaneous or intramuscular buprenorphine (0.01 to 0.02 mg/kg) every 12 hours thereafter as needed for analgesia.

All dogs were also given omeprazole 20 mg daily. Oral intake began 36 hours after surgery. Dogs were fed from an elevated/raised platform. Daily nutritional requirements were calculated and divided into 3 separate feedings. Gruel/soft food was provided for 1 week postoperatively followed by a gradual change to solid food over the ensuing 2-week period. The dogs were weighed weekly and housed in a run measuring approximately 10-14 feet to allow freedom to ambulate.

Endoscopic examinations were conducted 1 month post-operatively and immediately preceding euthanasia at 12 weeks to evaluate colon mucosal appearance and stricture. The temporal remodeling response was monitored using colonoscopy and biopsy collection. Animals were sacrificed at 2, 8, 10, or 12 weeks. Explants were stained with hematoxylin and eosin (H&E) and Alcian blue and were immunolabeled for proliferating cell nuclear antigen (PCNA). Gross analysis of explants showed that stricture formation occurred in the mucosectomy only dogs whereas none of the ECM treated dogs developed stricture. Histology showed that ECM promotes the reformation of site appropriate goblet cells and appropriately located PCNA+ proliferating cells. The mucosa of ECM treated dogs was nearly indistinguishable from native tissue whereas the mucosectomy only dogs showed no signs of new mucosal coverage Immediately after euthanasia, the scaffold placement site and the native colon tissue proximal and distal to the scaffold placement site were harvested. The excised segment was split longitudinally and the exposed mucosal surface was examined and photographed for dimensional measurements. The luminal circumference of the colon was measured 3 cm proximal to the superior edge of the remodeled site and in the middle of the graft to determine the extent of stenosis. Results were expressed as percent reduction of the circumference between the remodeled site and the proximal normal tissue (mean +/−SD).

The excised tissue was pinned to corkboard in a flattened position and immersed in 10% neutral buffered formalin. The specimen was trimmed longitudinally including both normal and remodeled tissue, sectioned, and stained with both hematoxylin-eosin and Masson's trichrome stains. The areas examined included the native tissue, the proximal and distal interfaces between the remodeled area and the native tissue, and the middle region of the remodeled area. On the basis of examination of the distributions of data, the data appear to be normally distributed. Thus, the statistical approach used to compare the results was the parametric t test (n=4).

The hypothesis tested was that the treatment of the EMR defect with SIS-ECM would cause less reduction in the circumference compared with no treatment. It is recognized that data from individual test animals were subjected to multiple statistical analyses (i.e., circumference reduction and weight.) The comparison of reduction in luminal circumference in the dogs was taken as the primary statistical analysis, which did not involve multiple testing. All other statistical tests are considered to be secondary with their P values stated uncorrected for repeated measures and should be taken as descriptive only.

RESULTS AND CONCLUSIONS

In the absence of treatment, scarring and stricture formation is expected outcome. However, ECM treatment resulted in mucosal coverage of the resected tissue that appeared normal grossly and microscopically. Outcomes varied slightly based on number of ECM layers in the tubular device—higher numbers of ECM layers were generally associated with increased mucosal coverage. No signs of stricture were present in any dogs treated with an ECM scaffold.

The current study in a dog model showed that a SIS-ECM scaffold, deployed endoscopically after circumferential EMR, facilitated colon mucosal remodeling (FIG. 1) without stricture formation. The remodeled tissue consisted of a completely epithelialized lumen with a dense, organized collagenous submucosa and normal-appearing muscularis externa.

Thus, these studies using a dog model and employing SIS-ECM grafts for regeneration of colon mucosal lining tissue demonstrate that ECM can be used in treating IBD, such as UC or CD.

Having thus described the invention it is clear that what may appear to be different embodiments could be provided without departing from the spirit and scope of the invention. Hence it is intended that the foregoing specification be interpreted as illustrative rather than in a limiting sense.

EXAMPLE 2

Application of Gel ECM for Replacement of Colon Tissue

In accordance with the invention, the feasibility of using an ECM gel composition for treatment of Inflammatory Bowel Disease (IBD) can be tested in vivo in rats. Rats may be established as a model for human IBD, such as Ulcerative Colitis (UC), whereby a UC-like inflammation can be induced in rat colon tissue by administering Dextran Sulfate Sodium (DSS) in drinking water ad libitum for several days.

Acute UC-like inflammation can be induced in rats by administering, in drinking water provided ad libitum, 5% DSS for seven days, followed by followed by administration of regular water. Chronic UC-like inflammation can be induced in rats by administering, in drinking water provided ad libitum, 5% DSS for one or more consecutive 7-day periods, followed by administration of regular water.

Treatment of UC can be carried out using a gel extracellular matrix (ECM) derived from small intestine submucosa (SIS) and introduced into the colon via enema. The gel SIS-ECM can be administered one or more times-per-day for a period of at least one week, and preferably up to about one month. A preferred dosing regimen for SIS ECM is once per day for 1-30 days.

Method of Preparation of Gels from ECM

The preparation of SIS from a segment of small intestine is detailed in U.S. Pat. Nos. 4,902,508, 5,275,826, and 5,514,533, the disclosures of which are expressly incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically, the SIS is rinsed with saline and optionally stored in a hydrated or dehydrated state until use as described below.

The present fluidized compositions are prepared as solutions or suspensions of intestinal submucosa by comminuting and/or digesting the submucosa with a protease, such as trypsin or pepsin, for a period of time sufficient to solubilize said tissue and form a substantially homogeneous solution. The intestinal submucosa starting material is comminuted by tearing, cutting, grinding, shearing and the like. Grinding the submucosa in a frozen or freeze-dried state is preferred although good results can be obtained as well by subjecting a suspension of pieces of the submucosa to treatment in a high speed (high shear) blender and dewatering, if necessary, by centrifuging and decanting excess water. The comminuted intestinal submucosa can be dried to form a submucosa powder. Thereafter, it can be hydrated, that is, combined with water or buffered saline and optionally other pharmaceutically acceptable excipients to form a tissue graft composition as a fluid having a viscosity of about 2 to about 300,000 cps at 25° C. The higher viscosity graft compositions can have a gel or paste consistency. The present compositions can be sterilized using art-recognized sterilization techniques such as exposure to ionizing radiation.

The fluidized submucosa of this invention also finds use as an injectable heterograft for tissues, for example, soft tissues, in need of repair or augmentation most typically to correct trauma or disease-induced tissue defects.

SIS Suspension

SIS specimens prepared as described above are minced or chopped into arbitrarily small pieces using tissue scissors, a single-edged razor blade, or other appropriate cutting implement. The specimens are placed in a flat bottom stainless steel container and liquid nitrogen is introduced into the container to freeze the specimens to prepare them for comminuting.

The frozen SIS specimens are then comminuted to form a coarse SIS powder. Such processing can be carried out, for example, with a Wiley mill or manual arbor press with a cylindrical brass ingot placed on top of the frozen specimens. The ingot serves as an interface between the specimens and the arbor press. Liquid nitrogen can be periodically added to the SIS specimens to keep them frozen.

Other methods for comminuting SIS specimens may be utilized to produce an SIS powder usable in accordance with the present invention. For example, SIS specimens can be freeze-dried and then ground using an arbor press or other grinding means. Alternatively, SIS can be processed in a high shear blender to produce, upon dewatering and drying, an SIS powder.

Further grinding of the SIS powder using a pre-chilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

SIS Solution

SIS powder is sifted through a wire mesh into any convenient vessel. The powder is then subjected to proteolytic digestion to form a substantially homogeneous solution. In one embodiment, the powder is digested with 1 mg/ml of pepsin (Sigma Chemical Co., St. Louis, Mo.) in 0.1 M acetic acid, adjusted to pH 2.5 with HCl, over a 48 hour period at room temperature. The reaction medium is neutralized with sodium hydroxide to inactivate the peptic activity. The solubilized submucosa may then be concentrated by salt precipitation of the solution and separated for further purification and/or freeze drying to form a protease solubilized intestinal submucosa in powder form.

The viscosity of fluidized submucosa compositions in accordance with this invention can be manipulated by controlling the concentration of the submucosa component and the degree of hydration. The viscosity can be adjusted to a range of about 2 to about 300,000 cps at 25° C. Low viscosity submucosa compositions are better adapted for intra-articular applications or applications within body cavities. Higher viscosity formulations, for example, gels, can be prepared from the SIS digest solutions by adjusting the pH of such solutions from about 6.0 to about 7.0. Gel forms of the present compositions, as submucosa suspensions or submucosa digest solutions, are typically preferred for subcutaneous or intramuscular applications using syringes or catheters.

SIS gel has also been described as being formed into a gel by mixing 0.1 N NaOH (1/10 of the volume of digest solution) and 10X PBS pH 7.4 (1/9 of the volume of digest solution) in appropriate amounts at 4° C. The solution was brought to the desired volume and concentration using cold (4° C.) 1× PBS pH 7.4 and placed in a 37° C. incubator for gelation to occur.

The ECM was able to form a matrix after 40 minutes in solution. The ECM-derived gel was liquid at temperatures below 20° C. but turns into a gel when the temperature is raised to 37° C.

In preparing gels from ECM, all of the solutions should be kept on ice and the following variables must be determined in accordance with U.S. Pat. No. 8,361,503, which is hereby incorporated by reference in its entirety:

Cf=concentration of the final gel in mg/ml
Cs=concentration of the ECM digest solution in ring/ml
$V_f$=volume of the final gel solution needed for the experiments
$V_d$=volume needed from the ECM digest solution in ml
$V_{10x}$=volume of 10X PBS needed in ml
$V_{1x}$=volume of 1X PBS needed in ml
$V_{NaOH}$=volume of 0.1 N NaOH needed in ml First, determine the final concentration (Cf) and volume (Vf) of ECM gel required. Then, calculate the mass of ECM needed by multiplying $C_f(mg/ml)*V_f(ml)$. This value will give you the volume needed from the ECM digest solution ($V_d$), where $V_d=[C_f(mg/ml)*V_f(ml)]/C_s$.

Calculate the volume of 10X PBS needed by dividing the calculated volume $V_d$ by 9 ($V_{10x}=V_d/9$). Calculate the volume of 0.1 N NaOH needed by dividing the calculated volume $V_d$ by 10 ($V_{NaOH}=V_d/10$). Calculate the amount of 1X PBS needed to bring the solution to the appropriate concentration/volume as follow: $V_{1x}=V_f-V_d-V_{10x}-V_{NaOH}$. Add all the reagents ($V_{1x}+V_d+V_{10x}+V_{NaOH}$) to an appropriate container (usually 15 or 50 ml centrifuge tubes) without the ECM digest ($V_d$). Place solutions on ice and keep on ice at all times.

Add the appropriate volume from the ECM digest solution ($V_d$) to the PBS/NaOH mixture prepared above and mix well with a 1 ml micropipette while being careful and avoiding the creation of air bubbles in the solution. Depending on the viscosity of the ECM digest solution, there might be some significant volume loss during the transfer. Monitor the total volume and add appropriate amounts until the final volume is achieved. Measure the pH of the pre-gel solution, where pH should be around 7.4.

Add the pre-gel solution to a mold or to appropriate wells. Place the mold or wells in a 37° C. incubator for a minimum of 40 minutes. Avoid using an incubator with $CO_2$ control. If water evaporation is a concern, place the mold inside a plastic zip-lock bag before placing in the incubator. After gelation, the gel can be removed from the mold and placed on 1X PBS. If the gels were made in tissue culture plates, 1X PBS can be placed on top of the gels until use to maintain the gels hydrated.

SIS-ECM Administration Procedure

SIS-ECM solution or suspension can be administered by enema into the colon of the UC-induced rats. No rejection, infection, or abnormal physiologic response of the host animal is expected following administration of the graft. The solution or suspension may also be administered via endoscopy and via laparoscopy into the colon. It is believed that an unexpected result of the current invention will be stimulation of appropriate tissue remodeling such that augmentation of colon mucosa can be accomplished with SIS solution or suspension material.

The fluidized compositions of this invention can result in tissue replacement and repair, and further result in treatment or cure of IBD, including UC. The fluidized submucosal compositions are used in accordance with the present method to induce regrowth of natural colon mucosal tissue. By injecting an effective amount of a fluidized ECM composition into the locale of the defective tissue, the biotropic properties can be realized without the need for more invasive surgical techniques.

EXAMPLE 3

In Vivo Study Using ECM Hydrogel (ECMH) For Remodeling of Colon Tissue in Rats

A nonsurgical and nonpharmacological approach to UC therapy can abate inflammatory flares by promoting alternative activation of the local innate immune cell population, and induce rapid replacement of colonic mucosal barrier function by restoring mucosal epithelial structure. The present study demonstrates efficacy of local delivery of a hydrogel form of mammalian extracellular matrix (ECMH) for treating UC. The effect of ECMH on clinical symptomology, inflammation, and epithelial barrier function was evaluated by multiple in-vivo and in-vitro outcome measures.

The study, presented in this Example, shows that an enema hydrogel composed of ECM effectively treats a rodent model of UC. Effective therapy was determined according to two essential physiologic processes that were positively directed by ECMH treatment: 1) restoration of colonic epithelial barrier function, which protects the host from the relentless barrage of pro-inflammatory luminal contents; and 2) resolution of the pro-inflammatory state of tissue macrophages, which propagate inflammation by releasing inflammatory cytokines. This strategy represents a proactive therapeutic approach and is a distinct departure from the immunosuppressive (defensive) and surgical (salvage) methods currently used to treat UC.

Unlike some previous reports, results of this study show that ECMH can mediate the innate immune inflammation response not by directly promoting an M2-like macrophage phenotype but by reducing the number or M1-like pro-inflammatory macrophages. The colons of ECMH treated animals do not have a reduction in macrophages (which are necessary mediators of tissue repair) but a reduction in inflammatory macrophages. Such immunomodulatory properties of ECMH, even used alone, can be as effective as current pharmacologic therapies without associated negative side effects. Additionally, ECMH therapy can have a protective effect on the epithelial cells of the colonic mucosa. This study demonstrates effective treatment of colonic inflammation with ECMH by restoring epithelial barrier function, mitigating pro-inflammatory macrophages and establishing the environment for mucosal tissue regeneration.

Methods

Experimental Design

To determine the efficacy and safety of ECMH in a validated UC rodent model, disease was induced in male Sprague Dawley rats and treated with a daily enema infusion for 7 consecutive days with either ECMH or Control solution mimicking the ECMH diluent including processing residuals. Animals were sacrificed at 7 days and 14 days post dextran sulfate sodium (DSS) to evaluate temporal response (n=14 per time point per treatment). Healthy rats, which did not receive DSS or enema infusions, were included for comparison at both 7 and 14 days (n=6 per time point). The primary study endpoints included clinical response, histologic scores, inflammation response, and barrier function. The effect of ECMH on inflammation and epithelial barrier function was measured in-vitro in lamina propria mononuclear cells (LPMC) and intestinal epithelial cells (IEC) respectively.

ECM Hydrogel Preparation and Formulations

Small intestinal submucosa (SIS) ECM was prepared from porcine small intestine. The intestine was harvested immediately following euthanasia, rinsed of contents in deionized water, and frozen. The tissue was thawed and the superficial layers of the tunica mucosa were mechanically removed. Likewise, the tunica serosa and tunica muscularis externa were mechanically removed, leaving the tunica submucosa and basilar portions of the tunica mucosa. The remaining SIS material was rinsed in deionized water for 24-72 h prior to treatment with 0.1% peracetic acid/4% ethanol and subsequent saline and water rinses. SIS-ECM was frozen, lyophilized, powdered with a Wiley Mill using a #60-mesh screen, and digested at 10 mg/mL dry weight with 1 mg/mL pepsin (Sigma, St. Louis, Mo.) in 0.01N HCl while stirring for 20-26 h at 21-23° C. Digest was stored in aliquots at −20° C. and neutralized prior to use. All in-vivo studies used an ECMH concentration of 8 mg/mL and all in-vitro studies used an ECMH concentration of 500 µg/mL.

$^{14}$C-labeled ECMH was prepared as stated above with the intestines of pigs that were injected with $^{14}$C-tagged proline, as previously described. FITC-labeled ECMH was prepared with a protein labeling kit per manufacturer's instructions (Thermo PierceNet; #53027).

Characterization of ECM Hydrogel

Decellularization efficiency was determined by the absence of nuclei in H&E and DAPI staining. Remnant DNA was measured via PicoGreen assay (Invitrogen) and DNA fragmentation was visualized using gel electrophoresis. Sulfated glycosaminoglycan content in the ECM was measured using a Blyscan Sulfated Glycosaminoglycan Assay (Biocolor Ltd.) per manufacturer's guidelines. The rheological characteristics of ECMH was determined with a rheometer (AR2000, TA instruments, New Castle, Del.) operating with a 40 mm parallel plate geometry and the steady shear viscosity was measured by applying a stress of 1 Pa at a frequency of 0.159 Hz, as described previously (reference). All characterization assays were completed on 4 independent preparations of ECM (n=4).

ECMH Adhesion Testing

The mucoadhesion of ECMH was measured using a modified detachment force measurement. A uniaxial tensile testing machine (MTS Insight; MTS Systems Corp., Eden Prairie, Minn.) equipped with a 10N load cell was used for all tensile strength measurements. Two colon sections were glued to steel washers (diameter 12.7 mm) with mucosa facing outward and one washer was glued to the bottom of a 24-well plate (diameter 15.6 mm). The ECMH was prepared by neutralizing with one tenth volume of 0.1M NaOH and one ninth volume of 10X PBS then 0.5 mL was added onto the bottom washer and the top washer was added and allowed to penetrate into the gel to a predetermined depth before incubating at 37° C. for 1 hour. After incubation, the mucosa was slowly withdrawn upwards at a constant speed of 5 mm/min until a failure occurred between the surfaces. Chickering & Mathiowitz (1995) (Kammer 1983).

Animals and Husbandry

All procedures and animal studies were approved and conducted in compliance with the University of Pittsburgh Radiation Safety Committee and the Institutional Animal Care and Use Committee. Male Sprague Dawley rats, 8-12 weeks of age, were obtained from Harlan and individually housed and environmentally acclimated for 7-10 days. Animals were housed under standard conditions with a temperature of 21-23° C. and 12 hr dark/light cycles. Rats were allowed ad libitum access to food and water throughout the study.

Disease Induction and Monitoring

Five percent dextran sulfate sodium (DSS) salt (36,000-50,000 MW; MP Biomedical) was prepared daily in deionized water and administered to rats by ad libitum drinking for 7 days and animals were monitored daily. Animal weight and consumption of food and water was tracked for each animal. Disease activity (i.e., stool consistency, presence of blood in stool, and weight loss) was measured every other day (i.e., days 1, 3, 5, 7, etc.) and scored on a range of 0 to 4 according to Table 1. Stool was scored by consistency (0=normal, 2=loose, 4=diarrhea) and presence of blood (0=none, 2=occult, 4=gross bleeding). Stool was tested for the presence of blood using ColoScreen ES Lab Pack Fecal Occult Tests. Weight loss compared to baseline was scored as follows: 0=none, 1=1-5%, 2=5-10%, 3=10-20%, and 4=>20%.

Enema Infusion Administration

Rats were anesthetized with 2-4% inhaled isoflurane and enema infusions were delivered using a flexible Surflo winged infusion catheter (Terumo, OD=2 mm). Enemas (5 mL) were administered at 3 sites along the colon utilizing a syringe attached to the catheter (approximately 1.6 mL per site), starting at 8 cm proximal to anus and at 5 cm and 3 cm while gradually removing the catheter with approximate total infusion time of 60 seconds (i.e., 20 sec per site).

ECMH Retention Studies With FITC- and $^{14}$C-ECMH

To determine hydrogel retention time, rats were administered FITC-labeled or $^{14}$C-labeled following disease induction with DSS. Eighteen rats were divided into 2 groups based on ECMH formulation (FITC- and $^{14}$C-ECMH) and sacrificed at 2 hr, 12 hr, and 24 hr post enema (n=3 per time point per ECMH formulation). Explanted colons from FITC-ECMH treated rats were processed to be optically clear such that the luminal contents were visible by fluorescent imaging. Immediately following sacrifice all samples were protected from light to prevent photo bleaching of the FITC conjugate. Optical clearing of the colons was initiated by incubating in Dent's fixative (1:4 dimethyl sulfoxide (DMSO): acetone) for 2 hours. Colons were then permeabilized and bleached in Dent's bleach (1:4:1 DMSO: acetone: $H_2O_2$) for 1 hour. Optically cleared colons were then imaged on a (Gel imager). Exposure time was set to a control sample of FITC-ECMH and kept constant for all subsequent images.

For $^{14}$C measurements, the entire colon of each rat was individually flash frozen and homogenized in liquid nitrogen. The tissue was ground with mortar and pestle and mixed until homogenous. Approximately 40 mg of tissue samples were analyzed by accelerated mass spectrometry (AMS). Non-treated controls were used to subtract the background $^{14}$C levels in native tissue.

Explanting and Scoring of Colonic Tissue

Animals were sacrificed at determined time points as described previously. Euthanasia was achieved by $CO_2$ inhalation and subsequent cervical dislocation in accordance with the American Veterinary Medical Association (AVMA). Following euthanasia, colon was resected via midline incision. A continuous colon segment was collected, spanning from the rectum to the cecum, and photographed. Colon length was measured as an indicator of disease activity. The colon was opened longitudinally and assessed grossly for damage. Scores were determined by investigators blinded to the treatment group.

The distal region of colon, 9 cm in length, was cut into thirds and opened longitudinally. Specimens were then collected for histology, ex-vivo organ culture, and myeloperoxidase measurement. The sections were paraffin embedded and sections (5 µm) obtained from 2 to 8 cm from distal to proximal colon were stained with hematoxylin and eosin (H&E) for representative histologic scoring. The distal and proximal portions were separated onto two slides and histologic scoring was performed by six blinded investigators.

TRITC-Dextran Permeability Assay

Intestinal permeability was assessed by enteral administration of TRITC-dextran (molecular mass 4.4 kDa; Sigma). Rats were administered TRITC-dextran (1 mL, 10 mg/mL) 4 h before sacrifice. Whole blood from cardiac juncture was obtained at the time of sacrifice and collected in serum tubes. TRITC-dextran measurements were performed in triplicate on a SpectraMax plate reader (Molecular Devices), with serial dilutions of TRITC-dextran used as a standard curve.

Organ Cultures

Full thickness biopsies were obtained from the colon of each experimental and control animal at day 7 and day 14 using a 3 mm dermal punch as described previously. Tissue specimens were cultured at 37° C. 5% CO¬2, 95% O2 for 48 hours. The supernatants were harvested and stored at −80° C. for TNF-α and PGE2 ELISA assays.

LPMC Isolation and Culture

LPMC were isolated from rats following colitis induction with 5% DSS in drinking water for 7 days as described above. The colon was explanted, cleared of mesenteric fat tissue, and regions of Peyer's patches were excised. The colon was then split in half longitudinally, cut into pieces, and dissociated into single cell suspensions using a lamina propria dissociation kit (Miltenyi) according to manufacturer's instructions. The suspension was then separated along a 40/70% Percoll gradient. The cells were suspended in RPMI 1640 containing 10% FBS and 100 U/mL penicillin and streptomycin and added to 96-well plates at 2×105 cells per well with or without the addition of 500 µg/mL ECMH and Control buffer. After incubation for 48 hours, the supernatant was collected and stored at −80° C. until ELISA assays when conducted for TNF-α and PGE2.

Intestinal Epithelial Cell (IEC) Culture

For in-vitro barrier function assays, IEC (Caco-2, passages 24-28, ATCC) were cultured to about 80% confluence in MEM containing non-essential amino acids, 1 mM sodium pyruvate, and 20% FBS. The functional response of IEC to ECMH was evaluated using rapid differentiation system (Corning Biocoat HTS Caco-2 Assay) per manufacturer's instructions. Confluent and differentiated cell monolayers were challenged with 100 ng/mL LPS for 2 hours and then treated with ECMH for 48 hours. The functional response of IEC was measured by transepithelial electrical resistance (TEER) and the presence of epithelial cadherin (E-cadherin) cell adhesion protein.

Transepithelial Electrical Resistance (TEER) Measurement

TEER of Caco-2 monolayers was measured routinely with an Epithelial Voltohmmeter (EVOM2, World Precision Instruments). Before seeding Caco-2 cells, electrical resistances of the supporting filter and buffer medium were measured and subtracted from the total electrical resistance determined with the monolayer to calculate the TEER of the monolayer. Only differentiated monolayers with TEER values greater than 300Ω×cm2 were used in the study.

Immunolabeling

To determine the macrophage response following ECMH treatment, paraffin embedded histologic sections were immunolabeled for indicators of the M1-like and M2-like macrophage phenotypes, TNF□ and CD206. Tissue sections were deparaffinized using xylene and rehydrated using a graded ethanol series. Heat-mediated antigen retrieval was performed using 0.001 M citrate buffer (pH=6) at 95° C. for 20 minutes. Tissue sections were subjected to Tris-Buffered Saline Tween-20 (TBST) for 15 min, followed by incubation in blocking buffer (2% horse serum/1% bovine serum albumin/0.05% tween-20/0.05% triton-x-100) for 1 hour. The primary antibodies, diluted in blocking buffer, were added to the slides for 16 h at 4 C in a humidified chamber. The slides were then washed three times in TBS prior to the addition of secondary antibody for 1 h in a humidified chamber at room temperature. Slides were counterstained with 4'6-diamidino-2-phenylindole (DAPI) to visualize nuclei. Primary antibodies used were mouse anti-rat CD68 (AbD Serotec, Raleigh, N.C.) at a 1:150 dilution as a pan macrophage marker, rabbit polyclonal to TNF□ (Abcam) at a 1:200 dilution as an M1-like marker, and goat polyclonal CD206 (Santa Cruz Biotech, Santa Cruz, Calif.) at a 1:100 dilution. The secondary antibodies used were Alexa Fluor donkey anti-mouse 594 (1:200, Invitrogen), Alexa Fluor donkey anti-goat 488 (1:200, Invitrogen), and Alexa Fluor donkey anti-rabbit 546 (1:200, Invitrogen). All primary antibodies were confirmed to cross-react with rat epitopes. Tissue sections were imaged at five random fields per tissue section. Quantification of markers was achieved using a custom image analysis algorithm developed using CellProfiler Image Analysis Software.

Statistical Analysis

Sample size was determined based on a power analysis using pilot study data in combination with previously published relevant studies. All animals were numbered and randomly assigned to a group. All investigators responsible for scoring were blinded to the experimental groupings. Quantitative outcomes were compared with a one-way or two-way analysis of variance (ANOVA) and post-hoc Tukey test to determine differences between groups. All statistical analysis was performed using SPSS Statistical Analysis Software (SPSS, IBM). Data are reported as mean±standard error unless otherwise stated.

Results

ECMH is Adhesive to Colon Tissue

Figure 12:
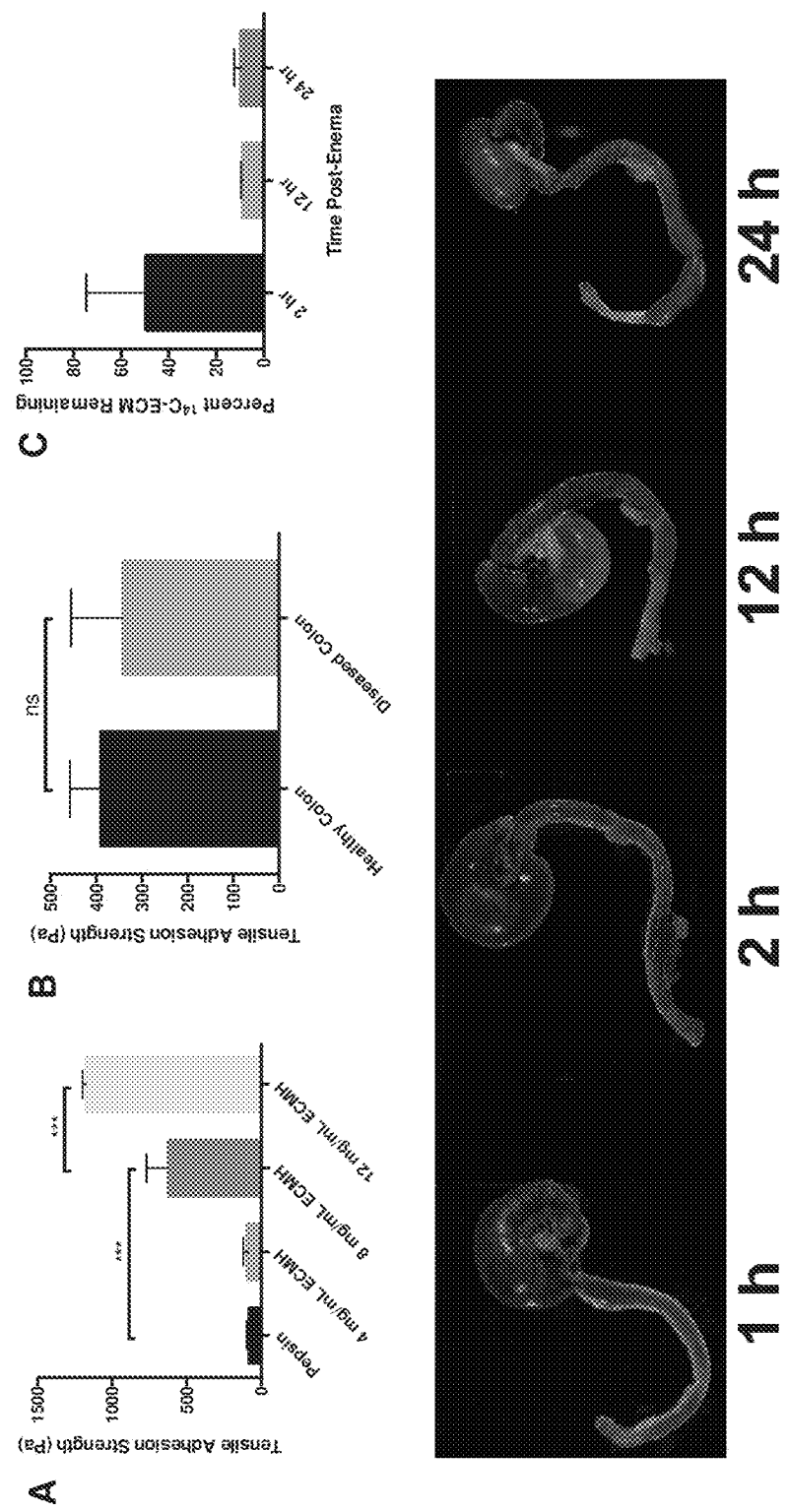

ECMH has the unique property of reverse thermal gelation and the hydrogel properties are dependent upon material characteristics. Enemas are routinely used in mild-to-moderate colitis as a basic form for targeted delivery to the inflamed colon. The therapeutic efficacy of ECMH is reliant upon its ability to adhere to the colon wall and interface with the inflamed cells. Results of adhesion testing show that ECMH is mucoadhesive, with a dose-dependent increase in adhesion strength when tested on healthy colon (FIG. 12A). The 8 mg/mL ECMH dose used in the study maintains equivalent adhesion strength in colitic rat colon when compared to healthy tissue (FIG. 12B). Mucosal adherence is not a property of all thermoreversible gels, as Pluronic F-127 (20%; Sigma) did not show adhesion strength greater than the negative control (data not shown). When delivered via enema to colitic rats, the residence time of the ECMH is greater than 24 hours. Two hours after administering the enema, ~50% of the $^{14}$C-ECMH remains and around 10% of the initial ECMH enema remains after 24 hours (FIG. 12C). These results were corroborated by visualization of FITC-ECMH (FIG. 12D). Together the findings demonstrate that ECMH material properties allow infusion as a liquid and the subsequent gelation ensures that the treatment remains localized for at least 24 hr. In accordance with the above findings, a daily enema treatment was used to measure the therapeutic efficacy of ECMH.

ECMH Treatment Mitigates Disease State

Figure 4:
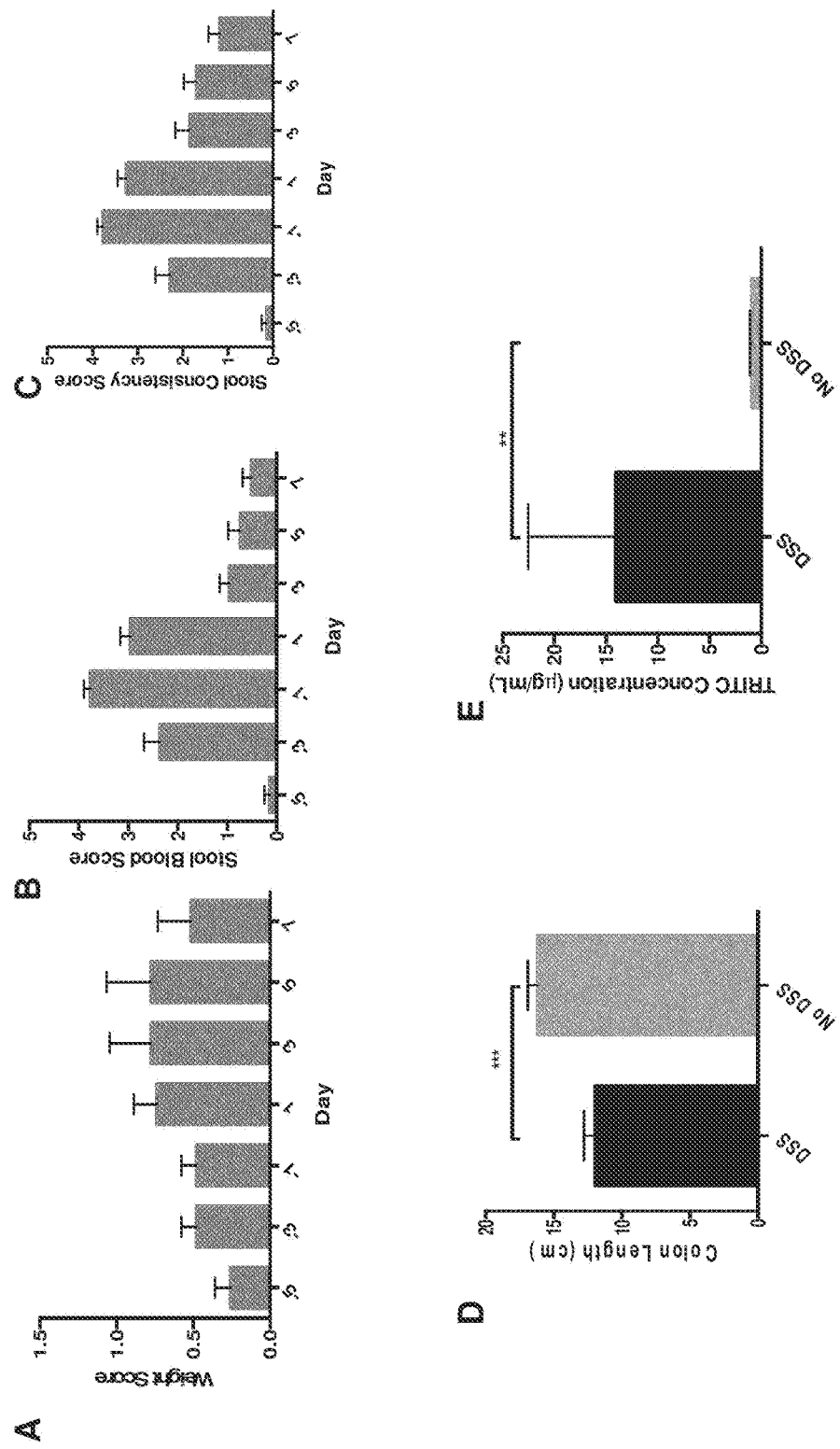
FIG. 4 shows the data supporting validation of the DSS model used, namely induction of disease state using 5% DSS in drinking water.
Figure 5:
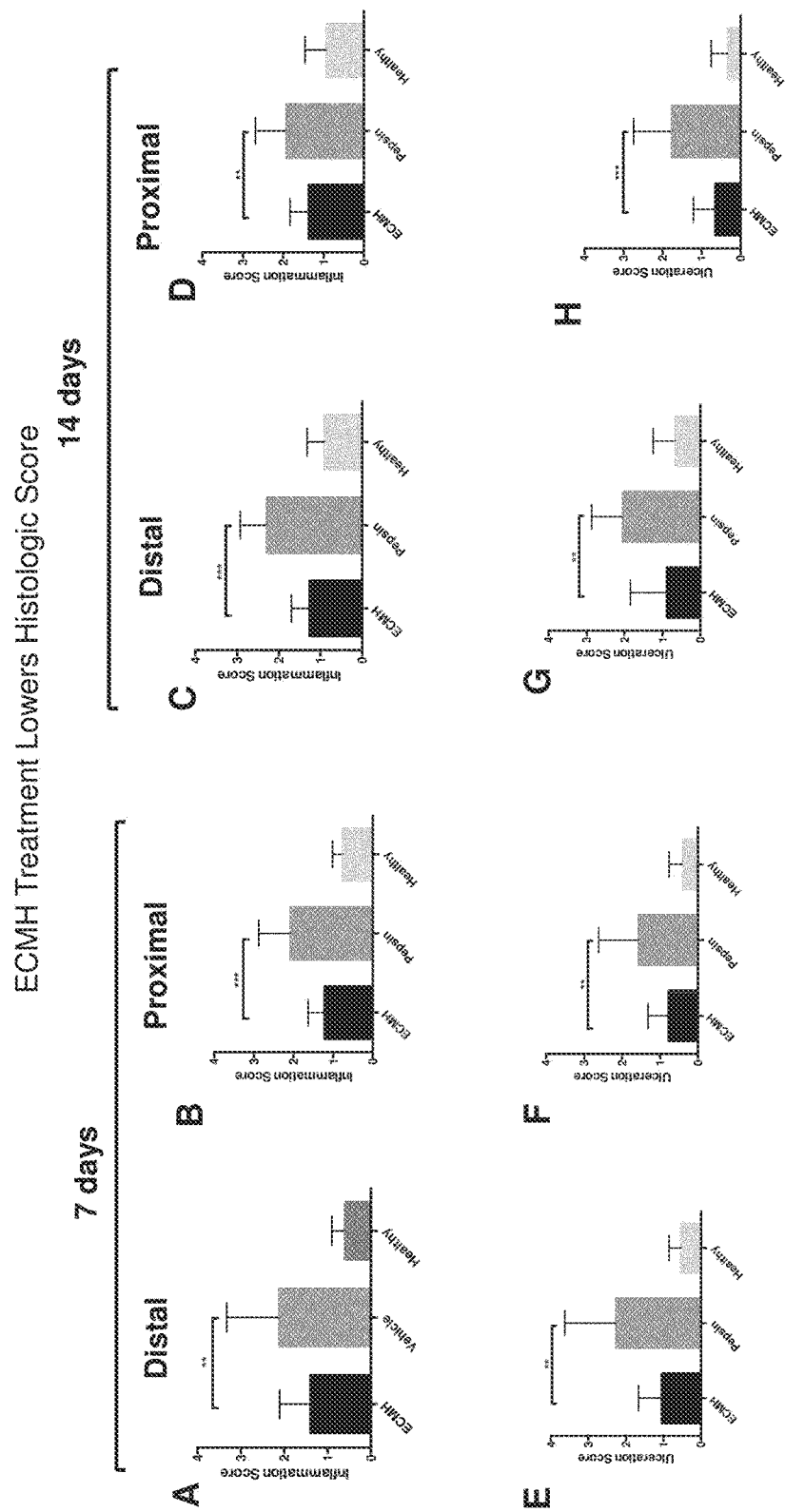
FIG. 5 shows histology results on the rat colons as described in Example 3, illustrating that ECMH treatment lowers histologic scores.
Figure 7:
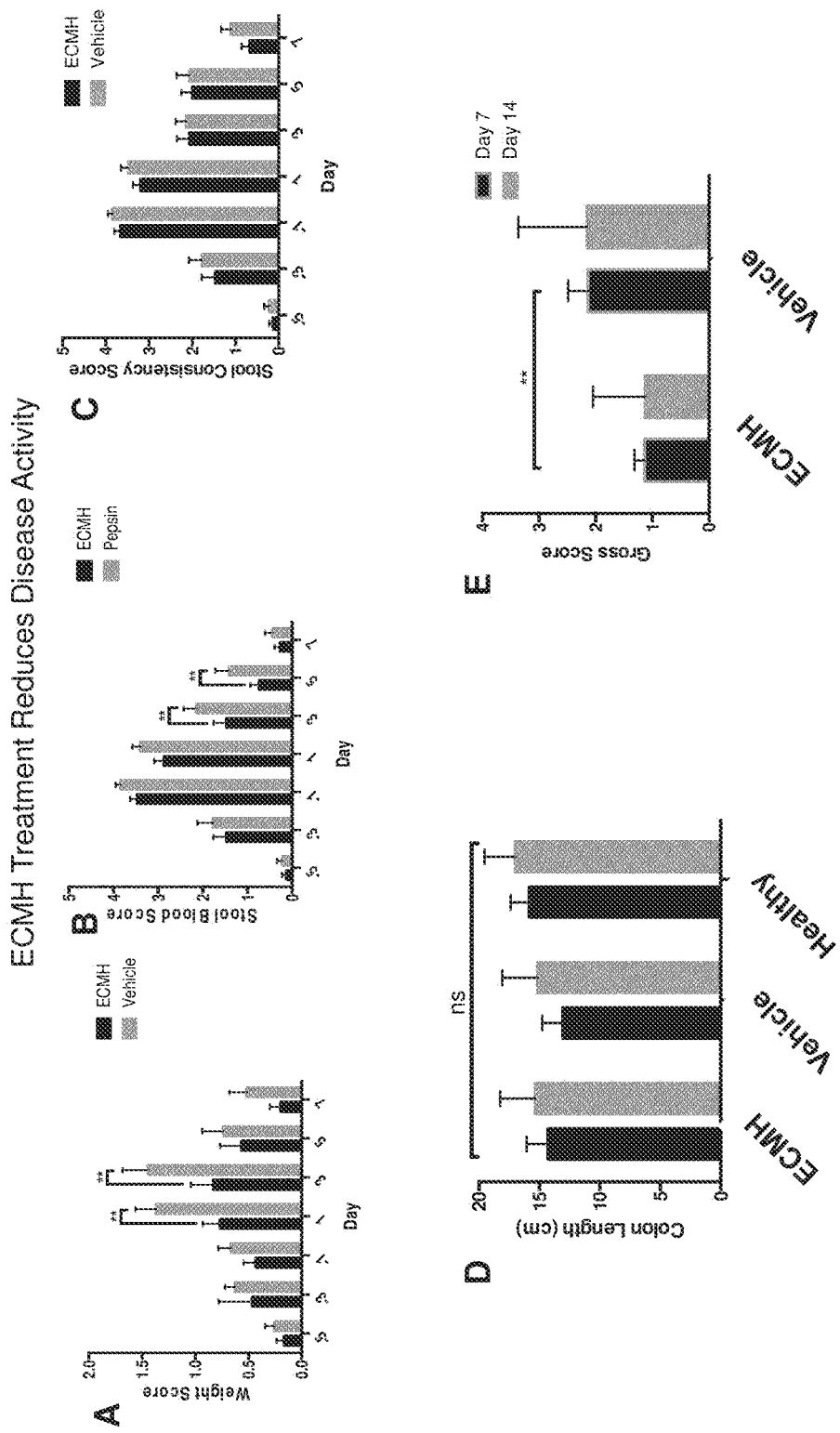
FIG. 7 shows clinical symptoms of disease results, illustrating that ECMH treatment reduces disease activity.

The DSS experimental model is a well-accepted UC-like self-limiting colitis phenotype with epithelial barrier defects. Clinical signs of colitis (e.g., weight loss, stool blood, and stool consistency) manifested following 3 days of exposure to 5% DSS in drinking water and reach their peak following 6 days (FIG. 4). ECMH treatment diminishes clinical symptoms of UC. Animals lose less weight (at days 1 and 3) and had less blood in stool (at days 3 and 5) compared to the Control. The shortening of the colon that was present at day 0 (FIG. 4D) but is no longer evident by days 7 and 14 across all groups (FIG. 8D). ECMH treatment results in a reduction in the colon gross anatomical score compared to the Control at day 7 (FIG. 8E). Histomorphologic analysis also showed that ECMH is therapeutic in the present model as evident in representative images (FIG. 6). ECMH treatment resulted in diminished signs of inflammation and lowered the degree of ulceration at 7 and 14 days in both distal and proximal tissue sections (FIG. 5). These data show that an ECMH enema infusion regimen effectively reduces clinical and histological signs of disease in a model of UC.

ECMH Restores Epithelial Barrier Function

Figure 13:
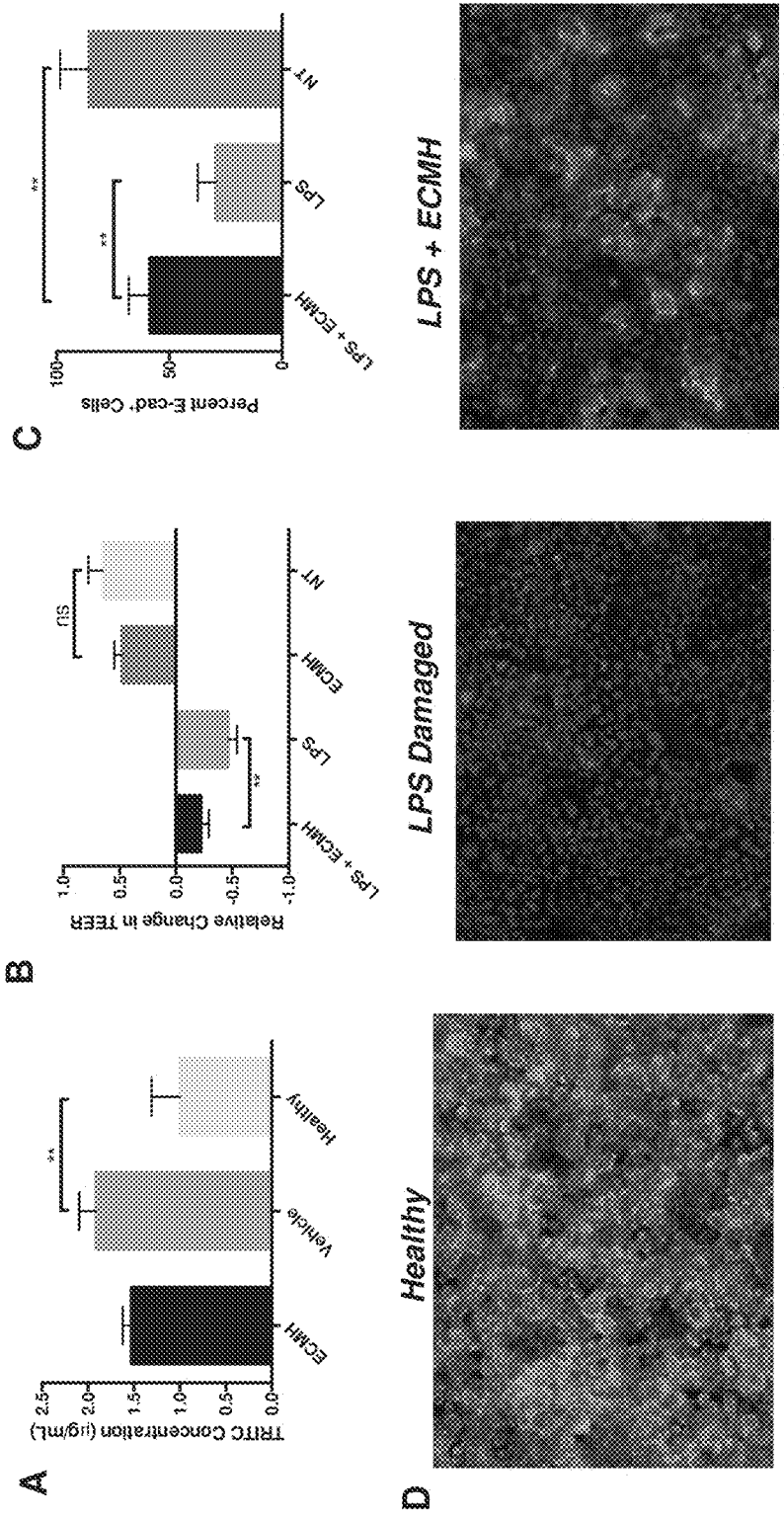
FIG. 13 shows barrier function is restored by ECMH administration.

The epithelial barrier in the colon can play an important role in disease progression. A defect in gut barrier function and increased permeability can lead to inflammatory bowel disease even in the presence of an intact immune system. Results of the TRITC-Dextran permeability assay showed that the barrier function of ECMH treated animals was similar to healthy animals at 7 days while the colonic epithelial barrier in the Control remained impaired compared to the healthy control (FIG. 13A). Differentiated and LPS-damaged monolayers of IEC respond to ECMH treatment with functional recovery as shown by TEER readings (FIG. 13B). The increased barrier function corresponds to an increased presence of E-cadherin, one of the most important cell-cell adhesion proteins in the gut. ECMH treatment leads to approximately 50% increase in E-cadherin positive cells compared with negative controls (FIG. 13C-D). These data show that ECMH facilitates functional improvement of the epithelial barrier function and that ECMH can act therapeutically by limiting epithelial cell damage or by actively salvaging mucosal integrity.

ECMH Role in Inflammation

Figure 11:
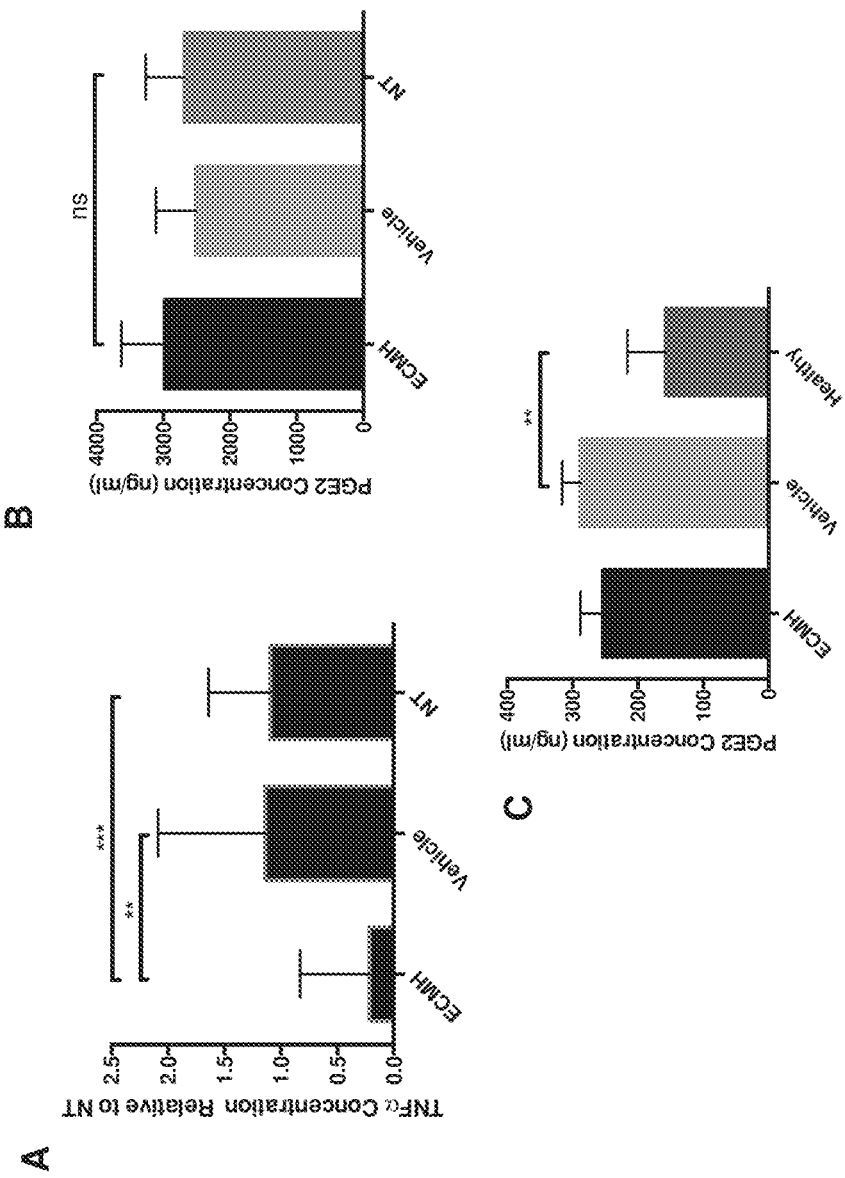
FIG. 11 shows graphic representation of inflammatory measures, illustrating that ECMH mediates inflammation.

Because inflammation can be part of the pathogenesis of UC, effective therapies mediate the inflammatory response. Inflammatory mediators of IBD (i.e., TNF-α and PGE2) were used to evaluate the effect of ECMH on inflammation. LPMC isolated from colitic rats were plated and exposed to ECMH. The ECMH treatment resulted in a substantial reduction in the production of TNF-α (FIG. 11A) by the LPMC but had no effect on PGE2 production (FIG. 11B). However, organ cultures collected from rats following the 1-week enema regimen of ECMH or Control showed secreted PGE2 was similar to healthy controls in the ECMH treated animals while the vehicle controls had significantly elevated levels of mucosal PGE2 (FIG. 11C). Secreted levels of TNF-a were below detection in the organ cultures regardless of experimental condition at the time points studied.

Figure 8:
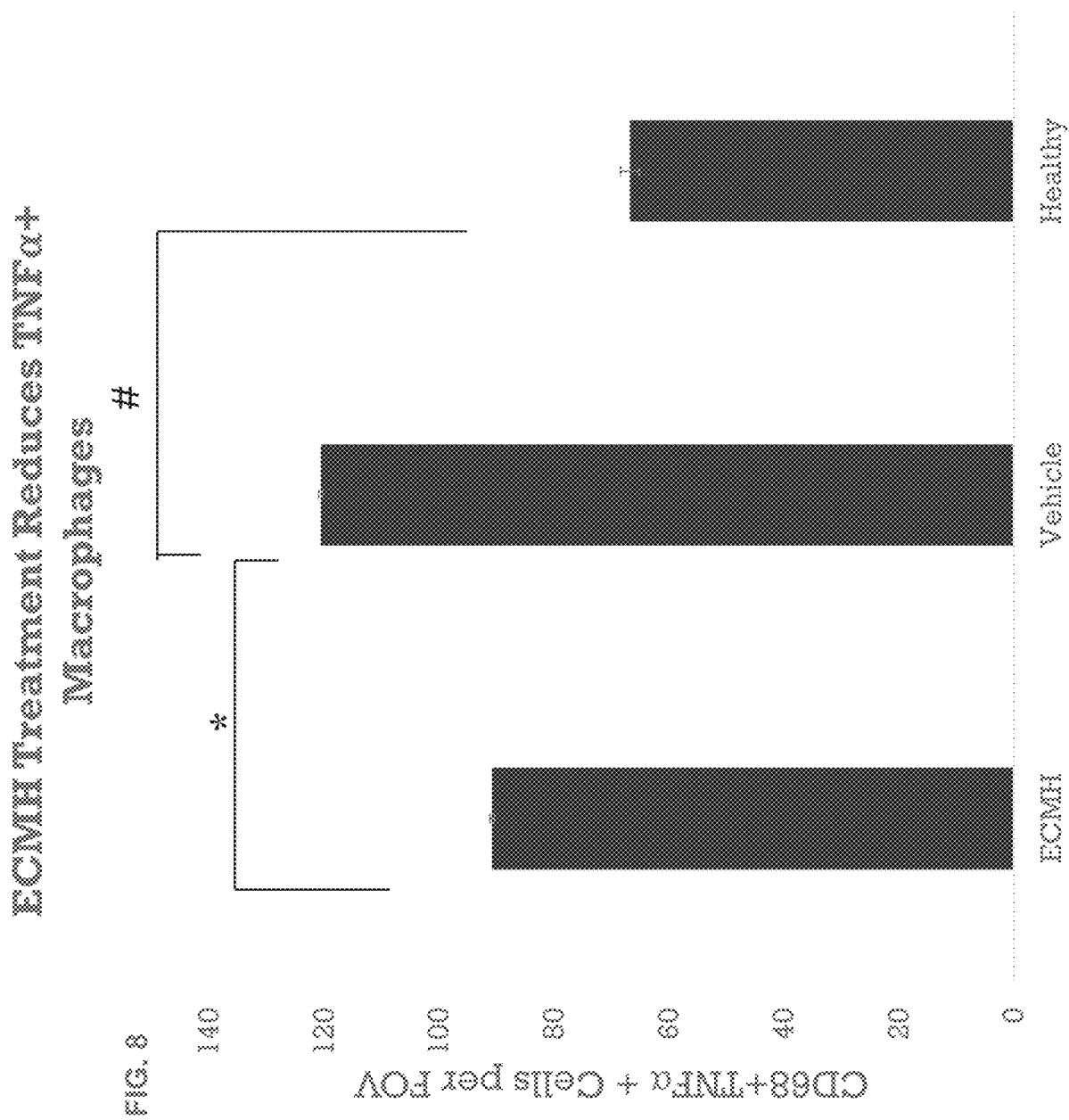
FIG. 8 is a graphic representation illustrating that ECMH treatment reduces TNFα+macrophages in ECMH-treated rats versus vehicle-treated sham rats and healthy (untreated) rats.
Figure 9:
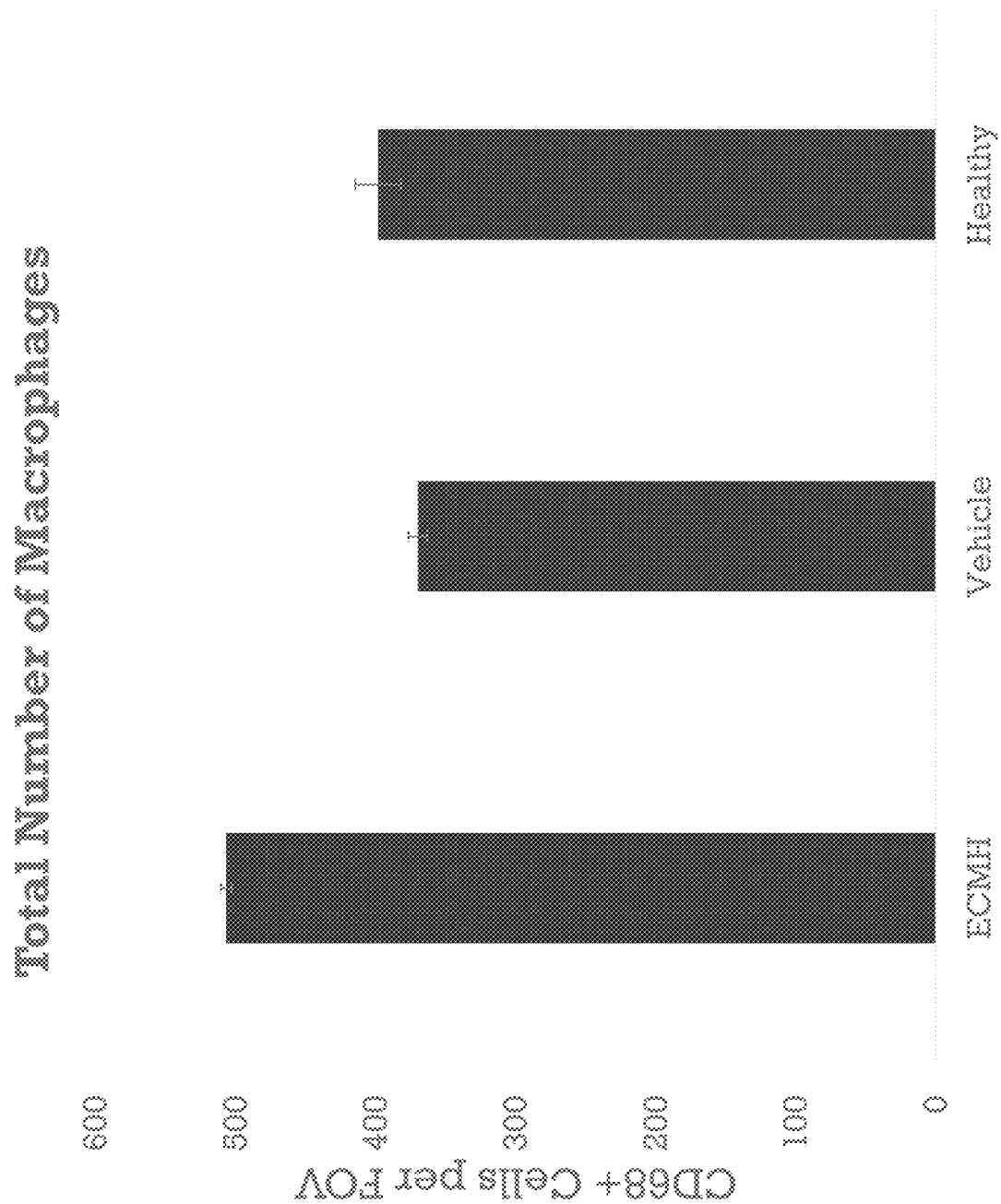
FIG. 9 shows a graph of total number of macrophages in ECMH-treated rats versus vehicle-treated rats and heathy (untreated) rats.
Figure 10:
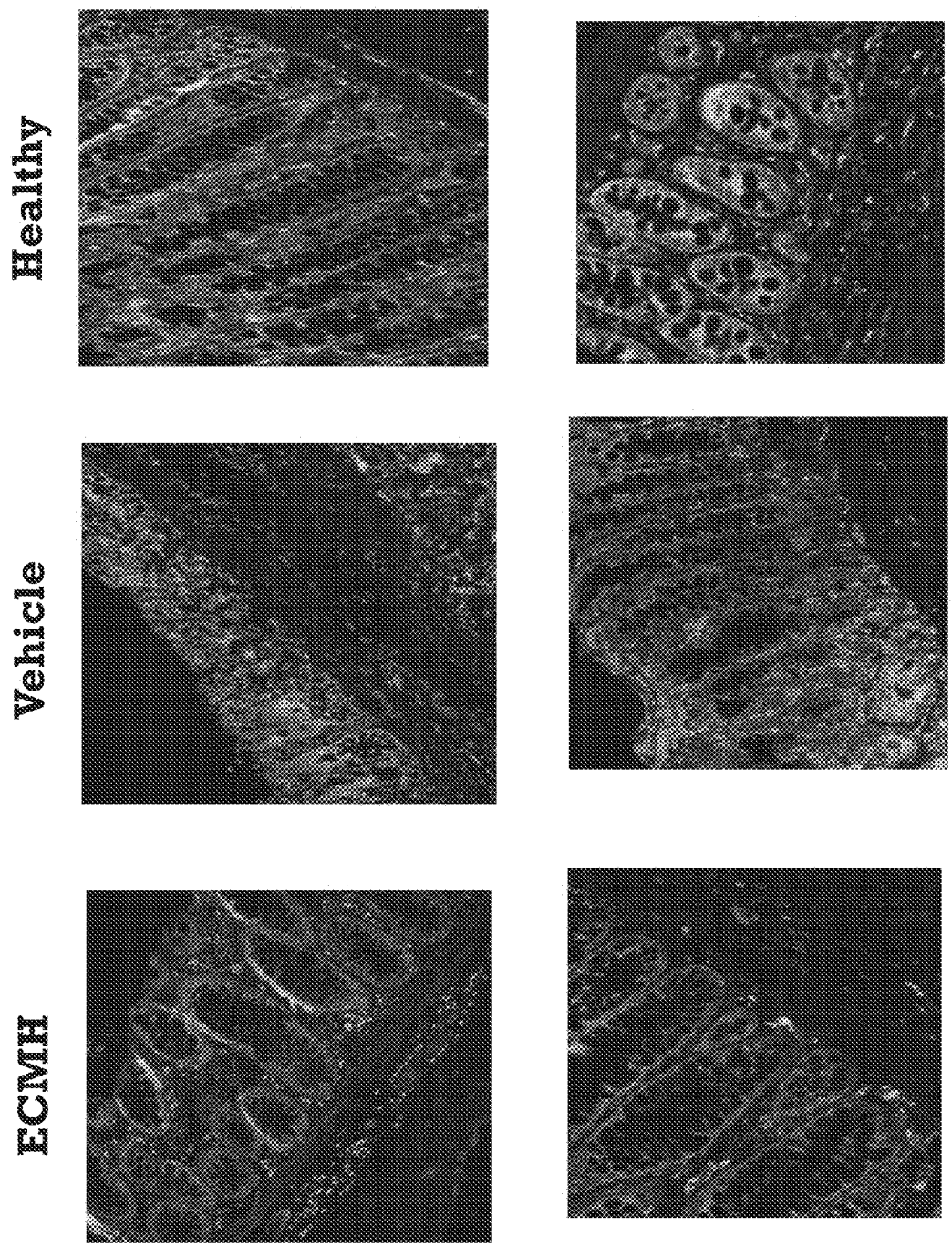
FIG. 10 shows representative images from tissue sections immunolabeled for macrophage phenotype markers from ECMH-treated vs. vehicle-treated sham vs. healthy rats.

The effect of ECMH on macrophage phenotype was evaluated by quantifying the number of CD68+ macrophages in the colon that co-express TNF-α or CD206 (see representative images in FIG. 10). Interestingly, the number of CD68+, CD206+, and TNF-α+ cells was the same across all treatment groups (FIG. 9), but ECMH treatment resulted in a reduction in the number of CD68+/TNF-α+ inflammatory macrophages at day 7 (FIG. 8). As ECMH did not affect the amount of global TNF-α+ cells but did reduce the number of CD68+/TNF-α+ cells, ECMH can have a direct role in modulating the macrophage response by reducing the number of inflammatory macrophages present in the colonic tissue.

Although the invention has been described in detail with reference to certain preferred embodiments, variations and modifications exist within the scope and spirit of the invention as described and defined in the following claims.

The invention claimed is:

1. A method for treating Inflammatory Bowel Disease (IBD) in a patient, said method comprising the steps of:
   providing an extracellular matrix hydrogel (ECMH) composition derived from tissue selected from the group consisting of large intestine, small intestine submucosa (SIS), and urinary bladder matrix (UBM), wherein the ECMH composition is a reverse thermal gel reconstituted from a lyophilized digest solution, wherein the ECMH composition is at a concentration which exhibits mucoadhesion in diseased tissue equivalent to mucoadhesion in healthy tissue and forms a barrier having a residence time up to 24 hours; and
   applying or administering the ECMH composition to intestinal tissue of the patient exhibiting IBD to induce in situ replacement of diseased or damaged tissue with healthy lower intestinal tissue.

2. The method of claim 1, wherein the IBD is selected from Ulcerative Colitis and Crohn's Disease.

3. The method of claim 2 wherein the application or administration of the ECMH composition stimulates migration of stem cells to the colon tissue, wherein the stem cells develop in situ to effect reconstructive tissue remodeling of the colon mucosal tissue exhibiting Ulcerative Colitis or Crohn's Disease.

4. The method of claim 1 wherein the ECMH composition is prepared as a fluidized gel, solution, or suspension.

5. The method of claim 1 wherein the ECMH is a solution or suspension administered by enema.

6. The method of claim 1 wherein the ECMH is a solution or suspension administered endoscopically.

7. The method of claim 1 wherein, prior to the application or administration step b), the method further comprises resecting or ablating diseased or damaged colon mucosal tissue.

8. The method of claim 7 wherein the resecting step comprises endoscopic mucosal resection (EMR) or ablation using EDTA.

9. The method of claim 1, wherein the method further comprises the optional steps selected from the group consisting of:
   creating an ileostomy in the patient, and
   feeding the patient intravenously using Total Parenteral Nutrition while new colon mucosa forms or develops.

\* \* \* \* \*